(12) United States Patent
Marciani

(10) Patent No.: US 7,196,073 B2
(45) Date of Patent: Mar. 27, 2007

(54) IMINE-FORMING POLYSACCHARIDE ADJUVANTS AND IMMUNOSTIMULANTS

(75) Inventor: Dante J. Marciani, Birmingham, AL (US)

(73) Assignee: Adjuvantys, Inc., New York, NY (US)

( * ) Notice: Subject to any disclaimer, the term of this patent is extended or adjusted under 35 U.S.C. 154(b) by 0 days.

(21) Appl. No.: 10/859,577

(22) Filed: Jun. 3, 2004

(65) Prior Publication Data

US 2004/0220142 A1 Nov. 4, 2004

Related U.S. Application Data

(62) Division of application No. 10/114,465, filed on Apr. 3, 2002, now Pat. No. 6,960,344, which is a division of application No. 09/165,310, filed on Oct. 2, 1998, now abandoned.

(60) Provisional application No. 60/060,786, filed on Oct. 3, 1997.

(51) Int. Cl.
*A61K 31/716* (2006.01)
*A61K 31/722* (2006.01)
*A61K 31/732* (2006.01)
*A61K 31/736* (2006.01)

(52) U.S. Cl. .......................... 514/54; 514/55; 514/56; 514/57; 514/58; 514/59; 514/60; 536/2; 536/55.1; 536/55.2; 536/123.1; 536/123.12

(58) Field of Classification Search ............ 514/54–60; 536/2, 55.1, 55.2, 123.1, 123.12
See application file for complete search history.

(56) References Cited

U.S. PATENT DOCUMENTS

| | | | |
|---|---|---|---|
| 3,236,792 A | 2/1966 | Curtis | |
| 3,297,604 A | 1/1967 | Germino | |
| 4,003,792 A | 1/1977 | Mill et al. | |
| 4,063,016 A | 12/1977 | Austin | |
| 4,115,305 A | 9/1978 | Hornby et al. | |
| 4,424,346 A | 1/1984 | Hall et al. | |
| 4,613,665 A | 9/1986 | Larm | |
| 4,663,448 A | 5/1987 | Chiu et al. | |
| 4,675,394 A | 6/1987 | Solarek et al. | |
| 4,693,891 A | 9/1987 | Collins et al. | |
| 4,695,624 A | 9/1987 | Marburg et al. | |
| 4,698,387 A | 10/1987 | Schmidt et al. | |
| 4,703,116 A | 10/1987 | Solarek et al. | |
| 4,731,162 A | 3/1988 | Solarek et al. | |
| 4,739,046 A | 4/1988 | Di Luzio | |
| 4,741,804 A | 5/1988 | Solarek et al. | |
| 4,749,800 A | 6/1988 | Jobe et al. | |
| 4,771,127 A | 9/1988 | Cryz et al. | |
| 4,795,745 A | 1/1989 | Larm et al. | |
| 4,801,699 A | 1/1989 | Solarek et al. | |
| 4,804,769 A | 2/1989 | Solarek et al. | |
| 4,895,724 A | 1/1990 | Cardinal et al. | |
| 4,983,748 A | 1/1991 | Tsai et al. | |
| 5,032,401 A | 7/1991 | Jamas et al. | |
| 5,057,503 A | 10/1991 | Czop et al. | |
| 5,110,909 A | 5/1992 | Dellacherie et al. | |
| 5,169,840 A | 12/1992 | Otterlei et al. | |
| 5,433,955 A * | 7/1995 | Bredehorst et al. ........ 424/94.3 |
| 5,508,310 A | 4/1996 | Rhodes | |
| 5,554,386 A | 9/1996 | Groman et al. | |
| 5,567,685 A | 10/1996 | Linden et al. | |
| 5,591,771 A | 1/1997 | Markonius | |
| 5,607,677 A * | 3/1997 | Jamas et al. ............. 424/278.1 |
| 5,624,914 A | 4/1997 | Patel et al. | |
| 5,668,193 A | 9/1997 | Gouda et al. | |
| 5,688,931 A * | 11/1997 | Nogusa et al. ................ 536/20 |
| 5,747,475 A | 5/1998 | Nordquist et al. | |
| 5,785,975 A | 7/1998 | Parikh et al. | |
| 5,912,000 A | 6/1999 | Podolski et al. | |
| 5,929,049 A | 7/1999 | Singh et al. | |
| 5,989,552 A | 11/1999 | McKenzie et al. | |
| 6,011,008 A * | 1/2000 | Domb et al. .................... 514/8 |
| 6,573,245 B1 * | 6/2003 | Marciani ..................... 514/25 |

FOREIGN PATENT DOCUMENTS

| | | |
|---|---|---|
| BR | 8202708 A | 12/1983 |
| EP | 0 320 942 A2 | 6/1989 |
| EP | 0 326 111 A2 | 8/1989 |
| EP | 0 477 508 A1 | 4/1992 |
| JP | 60-051702 | 3/1985 |
| JP | 06-166635 | 6/1994 |
| WO | WO 96/20012 A2 | 7/1996 |
| WO | WO 97/33612 A1 | 9/1997 |
| WO | WO 99/07744 A1 | 2/1999 |

OTHER PUBLICATIONS

Ambrosino, D.M., et al., "Effect of Haemophilus influenzae Polysaccharide Outer Membrane Protein Complex Conjugate Vaccine on Macrophages," *J. Immunol.* 149:3978-3983, The American Association of Immunologists (1992).

Apostolopoulos, V., et al., "Oxidative/reductive conjugation of mannan to antigen selects for $T_1$ or $T_2$ immune responses," *Proc. Natl. Acad. Sci. USA* 92:10128-10132, National Academy of Sciences (1995).

Apostolopoulos, V., et al., "Cell-mediated immune responses to MUC1 fusion protein coupled to mannan," *Vaccine* 14:930-938, Elsevier Science Ltd. (Jun. 1996).

Azuma, I., "Synthetic immunoadjuvants: application to non-specific host stimulation and potentiation of vaccine immunogenicity," *Vaccine* 10:1000-1006, Butterworth-Heineman Ltd. (1992).

(Continued)

*Primary Examiner*—Leigh C. Maier
(74) *Attorney, Agent, or Firm*—Sterne, Kessler, Goldstein & Fox P.L.L.C.

(57) ABSTRACT

The present invention relates to polysaccharide conjugates that comprise: a polysaccharide that binds to surface-receptors present on Antigen Presenting Cells, conjugated to one or more compounds having stable carbonyl groups covalently attached, either directly or via a bifunctional linker. The conjugates are useful as immuno-stimulants and adjuvants.

19 Claims, No Drawings

OTHER PUBLICATIONS

Barreto-Bergter, E. and Gorin, P.A.J., "Structural Chemistry of Polysaccharides from Fungi and Lichens," *Adv. Carbo. Chem. & Biochem.* 41:67-103, Academic Press, Inc. (1983).

Berger, L.R. and Reynolds, D.M., "The Chitinase System of a Strain of *Streptomyces Griseus*," *Biochim. et Biophys. Acta* 29:522-534, Elsevier Publishing Company (1958).

Bogwald, J., et al., "Coupling of polysaccharides activated by means of chloroacetaldehyde dimethyl acetyl to amines or proteins by reductive amination," *Carbohydrate Res.* 148:101-107, Elsevier Science Publishers B.V. (1986).

Bohn, J.A. and BeMiller, J.N., "(1→3)-β-D-Glucans as biological response modifiers: a review of structure-functional activity relationships," *Carbo. Poly.* 28:3-14, Elsevier Science Ltd. (1995).

Chang, R-C., and Shaw, J-F., "The immobilization of Candida cylindracea lipase on PVC, chitin and agarose," *Bot. Bull. Acad. Sinica* (Taiwan) 28:33-42, Taipei Academia Sinica. Institute Of Botany (1987).

Chen, H. and Rhodes, J., "Schiff base forming drugs: mechanisms of immune potentiation and therapeutic potential," *J. Mol. Med.* 74:497-504, Springer-Verlag (Sep. 1996).

Cryz Jr., S.J., et al., "Pseudomonas aeruginosa Immunotype 5 Polysaccharide-Toxin A Conjugate Vaccine," *Infect. Immun.* 52:161-165, American Society for Microbiology (1986).

Cryz, Jr., S.J., et al., "Pseudomonas aeruginosa Polysaccharide-Tetanus Toxoid Conjugate Vaccine: Safety and Immunogenicity in Humans," *J. Infect. Dis.* 154:682-688, The University of Chicago (1986).

Cryz, Jr., S.J., et al., "Vaccine Potential of Pseudomonas aeruginosa O-Polysaccharide-Toxin A Conjugates," *Infect. Immun.* 55:1547-1551, American Society for Microbiology (1987).

Cryz Jr., S.J., et al., "Octavalent Pseudomonas aeruginosa O-polysaccharide-toxin A conjugate vaccine," *Microb. Pathog.* 6:75-80, Academic Press, Ltd. (1989).

Cui, H., et al., "Cyclodextrin glucotransferase immobilized on konjac glucomannan," *Tiaran Chanwu Yanjiu Yu Kaifa* 5:48-54, Chengtu Chin Int. Book Trading Corp. (1993).

Dalsgaard, K., "A Study of the Isolation and Characterization of the Saponin Quil A. Evaluation of Its Adjuvant Activity, With a Special Reference to the Application in the Vaccination of Cattle Against Foot-and-Mouth Disease," *Acta Vet. Scand. Suppl.* 69, 19:1-40, Danske Dyrlaegeforengin (1978).

Dellacherie, E., and Bonneaux, F., "A new approach to aldehydic dextrans," *Polym. Bull.* 31:145-149, Springer-Verlag (1993).

Erlanger, B.F., et al., "Steroid-Protein Conjugates. I. Preparation and Characterization of Conjugates of Bovine Serum Albumin with Testosterone and With Cortisone," *J. Biol. Chem.* 228:713-727, The American Society of Biological Chemists, Inc. (1957).

Good, A.H., et al., "Identification of Carbohydrate Structures That Bind Human Antiporcine Antibodies: Implications for Discordant Xenografting in Humans," *Transplant. Proc.* 24:559-562, Elsevier Science, Inc. (1992).

Hahn, M.G. and Albersheim, P., "Host-Pathogen Interactions. XIV. Isolation and Partial Characterization of an Elicitor from Yeast Extract," *Plant Physiol.* 62:107-111, American Society for Plant Physiologists (1978).

Inman, J.K., "Thymus-Independent Antigens: The Preparation of Covalent, Hapten-Ficoll Conjugates," *J. Immunol.* 114:704-709, The Williams & Wilkins Co. (1975).

Janusz, M.J., et al., "Isolation of Soluble Yeast β-Glucans that Inhibit Human Monocyte Phagocytosis Mediated By β-Glucan Receptors," *J. Immunol.* 137:3270-3276, The American Association of Immunologists (1986).

Jiang, W., et al., "The receptor DEC-205 expressed by dendritic cells and thymic epithelial cells is involved in antigen processing," *Nature* 375:151-155, Macmillan Publishers, Ltd. (1995).

Jing, S-B., et al., "Water absorption of chitosan crosslinked by formaldehyde," *Kichin Kitosan Kenkyu* 1:106-107, Shibayama-machi, Chiba (1995).

Kobayashi, M., and Ichishima, E., Application of periodate oxidized glucans to biochemical reactions, *J. Carbohydrate Chem.* 10:635-644, Marcel Dekker, Inc. (1991).

Kolar, C., et al., "Preparation and Use of Synthetic Blood Group Specific Immunoadsorbents," *Behring Inst. Mitt.* 82:94-103, Die Medizinische Verlagsgesellschaft mbH (1988).

Kumar, T.S., and Rao, K.P., "Biodegradable chitosan microspheres: a potential carrier for antigens," *Macromolecules—New Front. Proc. IUPAC Int. Symp. Adv. Polm. Sci. Tech.* 2:657-661, Allied Publ. Ltd. (1998).

Lagergard, T., et al., Synthesis and Immunological Properties of Conjugates Composed of Group B Streptococcus Type III Capsular Polysaccharide Covalently Bound to Tetanus Toxoid, *Infect. Immun.* 58:687-694, American Society of Microbiology (1990).

Lett, E., et al., Immunogenicity of Polysaccharides Conjugated to Peptides Containing T- and B-Cell Epitopes, *Infect. Immun.* 62:785-792, American Society for Microbiology (1994).

Lett, E., et al., "Mucosal Immunogenicity of Polysaccharides Conjugated to a Peptide or Multiple-Antigen Peptide Containing T- and B-Cell Epitopes," *Infect. Immun.* 63:2645-2651, American Society for Microbiology (1995).

Lillo, L.E., and Matsuhiro, B., "Chemical modifications of carboxylated chitosan," *Carbohydrate Polym.* 34:397-401, Elsevier Science, Ltd. (Dec. 1997).

Lu, C., et al., "Chitin as a solid phase carrier to detect hepatitis B surface antigen," *Shengwu Huaxue Yu Shengwu Wuli Jinzhan* 19:454-456, Beijing da xue chu ban ske (1992).

Maron, E., et al., "Immunological Studies of Affinity Labelled Hen Egg-White Lysozyme and of the Active Site Region of Related Lysozymes," *Biochim. et Biophys. Acta* 278:243-249, Elsevier (1972).

Murata, J.-i., et al., "Synthesis of muramyl dipeptide analogue-glucomannan conjugate and its stimulation activity against macrophage-like cells," *Carbohydrate Polymers* 29:111-118, Elsevier Science, Ltd. (Feb. 1996).

Nilsson, K., et al., "*p*-Toluenesulfonyl Chloride as an Activating Agent of Agarose for the Preparation of Immobilized Affinity Ligands and Proteins. Optimization of Conditions for Activation and Coupling," *Acta Chem. Scand. B* 35:19-27, Munksgaard International Publishers (1981).

Nilsson, K. and Mosbach, K., "Immobilization of Ligands with Organic Sulfonyl Chlorides," *Meth. Enzymol.* 104:56-69, Academic Press Inc. (1984).

Ohta, M., et al., "Contribution of the mannan O side-chains to the adjuvant action of lipopolysaccharides," *Immunol.* 60:503-507, Blackwell Scientific Publications Ltd. (1987).

Ohya, Y., et al., Synthesis of a MDP Analogue/Chitin Conjugate That Stimulates Cultures Macrophages, *J. Bioactive & Compatible Polymers* 8:351-364, Technomic Publishing Co., Inc. (1993).

Ohya, Y., et al., "Preparation of chitosan and mannan derivatives having carboxylic acid groups by periodate oxidation and their function," *Kichin Kitosan Kenkyu* 1:114-115, Shibayama-machi, Chiba (1995).

Okawa, Y., et al., "Production of anti-peptide specific antibody in mice following immunization with peptides conjugated to mannan," *J. Immunol. Meth.* 149:127-131, Elsevier Science Publishers B.V. (1992).

Ouchi, T., et al., Design of D-glucose analogue of MDP/CM-polysaccharide Conjugates exhibiting macrophage activities, in *Anaheim. Book of Abstracts*, 209th ACS National Meeting, Anaheim, CA, Apr. 2-6, 1995, Abstract No. 043, P. CELL, American Chemical Society (1995).

Paz, M.A., et al., "Determination of Carbonyl Compounds with N-Methyl Benzothiazolone Hydrazone," *Arch. Biochem. Biophys.* 109:548-559, Academic Press (1965).

Portera, C.A., et al., "Effect of macrophage stimulation on collagen biosynthesis in the healing wound," *Am. Surg.* 63:125-131, Southeastern Surgical Congress (Feb. 1997).

Rhodes, J., et al., "Therapeutic potentiation of the immune system by costimulatory Schiff-base-forming drugs," *Nature* 377:71-75, Nature Publishing Group (1995).

Rhodes, J., "Covalent chemical events in immune induction: fundamental and therapeutic aspects," *Immunol. Today* 17:436-441, Elsevier Science Ltd. (Sep. 1996).

Rioux, S., et al., "Evaluation of Protective Efficacy of an Actinobacillus Pleuropneumoniae Serotype 1 Lipopolysaccharide- Protein Conjugate in Mice," *Comp. Immun. Microbiol. Infect. Dis.* 20:63-74, Els vier Science, Ltd. (Jan. 1997).

Sela, M., "Antigenicity: Some Molecular Aspects," *Science* 166:1365-1374, American Association for the Advancement of Science (1969).

Senju, R. and Okimasu, S., "Studies on Chitin. Part I. On the Glycolation of Chitin and the Chemical Structure of Glycol Chitin," *J. Agricult. Chem. Soc. Jap.* 22:432-437, Nippon Nogei Kaggakai (1948).

Stahl, P.D., The mannose receptor and other macrophage lectins, *Curr. Opin. Immunol.* 4:49-52, Current Biology, Ltd. (1992).

Vinogradov, E., et al., "Structural analysis of the intact polysaccharide mannan from *Saccharomyces cerevisiae* yeast using $^1$H and $^{13}$C NMR spectroscopy at 750 MHz," *Carbo. Res.* 307:177-183, Elsevier Science Ltd. (Feb. 1998).

Yamada, H., et al., "Structural Characterization and Antitumor Activity of a Pectic Polysaccharide from the Roots of *Angelica acutiloba*," *Planta Med.* 56:182-186, Georg Thieme Verlag (1990).

Zheng, B., et al., "Galactose Oxidation in the Design of Immunogenic Vaccines," *Science* 256:1560-1563, American Association for the Advancement of Science (1992).

Biochemistry Labfax, Chambers, J.A.A., and D. Rickwood, eds., Bios Scientific Publishers, Ltd., Oxf rd, UK, pp. 310,312 (1993).

McGraw-Hill Dictionary of Chemical Terms, Parker, S.P., ed., McGraw-Hill Companies, USA, (1985) (1st page of "M section").

"Nomenclature of Carbohydrates," from IUPAC-IUBMB Joint Commission on Biochemical Nomenclature (JCBN) at www.chem.qmul.ac.uk/iupac/2carb/ (Recommendations 1996).

International Search Report for International Application No. PCT/US98/20660 mailed on Jan. 28, 1999.

Supplementary European Search Report for European Application No. 98 94 9701 completed on Oct. 18, 2000.

Caplus (Patent Focus), Accession No. 1984:450822, Caplus English language abstract for BR 8202708. (Document AL1).

Patent Abstracts of Japan, vol. 9, No. 184 (C-294), Jul. 30, 1985, English language abstract for JP 60-051702. (Document AM1).

Patent Abstracts of Japan, vol. 18, No. 495 (C-1250), Sep. 16, 1994, English language abstract for JP 06-166635. (Document AL2).

Caplus, Accession No. 1994:186102, Caplus English language abstract for Cui, H., et al., "Cyclodextrin glucotransferase immobilized on konjac glucomannan," *Tiaran Chanwu Yanjiu Yu Kaifa* 5:48-54 (1993) (Document AT5).

Caplus, Accession No. 1997:135817, Caplus English language abstract for Jing, S-B., et al., "Water absorption of chitosan crosslinked by formaldehyde," *Kichin Kitosan Kenkyu* 1:106-107 (1995) (Document AT8).

Caplus, Accession No. 1998:286437, Caplus English language abstract for Kumar, T.S., and Rao, K.P., "Biodegradable chitisan microspheres: a potential carrier for antigens," Macromolecules—New Front. Proc. IUPAC Int. Symp. Adv. Polm. Sci. Tech. 2:657-661, Allied Publ., Ltd. (1998) (Document AT9).

Caplus, Accession No. 1993:467090, Caplus English language abstract for Lu, C. et al., "Chitin as a solid phase carrier to detect hepatitis B surface antigen," Shengwu Huaxue Yu Shengwu Wuli Jinzhan 19:454-456 (1992) (Document AS11).

Caplus, Accession No. 1997:135844, Caplus English language abstract for Ohya, Y., et al., "Preparation of chitosan and mannan derivatives having carboxylic acid groups by periodate oxidation and their function," *Kichin Kitosan Kenkyu* 1:114-115 (1995) (Document AT13).

English language abstract of IL 103446, Cohen, Z. and Rapaport, P.O.B., "Lipophilic Oligosacchari d Antibiotic Salt Compositions," published Oct. 15, 1992, pp. 3098-3099 (Feb. 1997).

\* cited by examiner

IMINE-FORMING POLYSACCHARIDE ADJUVANTS AND IMMUNOSTIMULANTS

CROSS-REFERENCE TO RELATED APPLICATIONS

This application is a divisional of U.S. patent application Ser. No. 10/114,465, filed Apr. 3, 2002 now U.S. Pat. No. 6,960,344, which is a divisional of U.S. patent application Ser. No. 09/165,310, filed Oct. 2, 1998 now abandoned, which application claims the benefit of earlier filed U.S. provisional patent application No. 60/060,768, filed Oct. 3, 1997, the contents of which are fully incorporated by reference herein.

BACKGROUND OF THE INVENTION

1. Field of the Invention

The present invention is related to the use of polysaccharide derivatives in vaccines and immunostimulating compositions. The adjuvants are derivatives of polysaccharides recognized by antigen presenting cells (APCs).

2. Related Art

Adjuvants have utility in activating the immune system to increase the efficacy of preventative and therapeutic vaccines. Immunoadjuvants have applications in: (1) the non-specific stimulation of host resistance against infection and cancer, (2) the potentiation of preventative vaccine immunogenicity, and (3) the potentiation of therapeutic vaccine immunogenicity. These adjuvants may preferentially enhance cell-mediated immune responses (T cell responses, delayed hypersensitivity), humoral responses (B cell responses, antibody production), or both. Stimulation of humoral immunity is important for prevention of bacterial infections, some viral infections, as well as in therapy of circulating cancers. Cellular immunity is of major importance for solid tumor cancer therapy and some viral diseases.

After an initial stimulation by a foreign agent or antigen (such as viruses, bacteria, or parasites), the immune system usually recognizes and reacts to the agent with an accelerated response upon re-exposure. This enhanced response forms the basis for the enormous success of vaccination for disease prevention. However, the initial immune response to a foreign antigen requires several days for full response, which is insufficient for protection against infections by highly virulent organisms. A way to achieve a faster protective immune response is by vaccination or immunization with a pathogen, which is usually attenuated or dead. However, in many cases immunization with killed microorganisms or with pure antigens elicits a poor short term immune response with weak or no cell-mediated immunity produced at all. In many cases this poor immune response can be modified by the addition of adjuvants to the antigen preparation. Several polysaccharides (carbohydrate polymers) of mannose (e.g. mannans), β(1,3) glucose (e.g. glucans), β(1,4) acetylated mannose (acemannans), β(1,4) N-acetyl-glucosamine (chitins), and heteropolysaccharides, such as rhamnogalacturonans (pectins), have been shown to stimulate the immune system. Antigen presenting cells (APCs) have specific cell-surface-receptors which recognize and bind the sugar moieties of these and other polysaccharides. Antigen presenting cells (APCs), such as dendritic cells and some macrophages, are responsible for taking up antigens and processing them to small peptides in endolysosomes. Processed antigens are expressed on the surface of APCs in conjunction with class II MHC. Specifically, reactive T cells recognize antigen and class II MHC simultaneously, yielding immune responses that are class II MHC restricted. B cells are stimulated by processed antigens to produce antibodies. These APC surface-receptors (such as the macrophage mannose receptor and its homologous receptor DEC-205 from dendritic cells) are trans-membrane proteins that mediate endocytosis and apparently play a role in the process of antigen presentation (Stahl, P.D., *Current Opinion in Immunology* 4:49 (1992); Jiang, W., et al., *Nature* 375:151 (1995)). Binding of these polysaccharides to such receptors apparently induces immunostimulation, as shown by the increase in phagocytosis, proliferative responses, release of cytokines, and other activities of the immune system. Because of this immunostimulatory activity, these polysaccharides have been proposed as vaccine adjuvants.

Polysaccharide adjuvants exert an immunomodulating effect by modifying cytokine production, such as upregulating IL-1, and causing a moderate Th1 response. The immune response produced by the Th1 subset of $CD4^+$ T cells induces complement fixing antibodies as well as strong, delayed-type hypersensitivity (DTH) reactions associated with γ-IFN, IL-2 and IL-12. Polysaccharides' effects on the native protein conformation are moderate, preserving the conformational epitopes necessary to elicit a neutralizing antibody response. However, because these adjuvants cannot allow exogenous antigens to be processed via the endogenous pathway, they do not induce a cytotoxic T lymphocyte (CTL) response. Because APCs have cell-surface-receptors specific for certain carbohydrate moieties, the targeting and delivery to these cells of antigens associated with these sugar moieties can be significantly enhanced. Apparently, the role of sugar moieties in the targeting of antigen delivery is not limited to polysaccharide adjuvants. For instance, the modification of quillajasaponin carbohydrate side-chains by periodic acid oxidation results in a loss of their adjuvanticity. Presumably, this results because of the loss of their targeting capacity.

Although the adjuvant properties of certain polysaccharides have been known for some time, their use has been largely limited to research applications. For instance, it has been shown that glucans can induce an anti-tumor response in mice, and have a preventive effect on acute sepsis. These effects are dependent on the glucans' molecular weight and their degree of branching. Mannans are other polysaccharides with adjuvant activity which presumably exert their effect after binding to the macrophage mannose cell-surface-receptor. Recently, it has been shown that conjugation of a protein antigen to mannan under oxidizing conditions resulted in a cell-mediated immune response (Apostolopoulos, V. et al., *Vaccine* 14: 930 (1996)). However, protein antigens conjugated to mannans under non-oxidative conditions, i.e. without aldehyde formation, elicited only humoral immunity (Okawa, Y. et al., *J. Immunol. Meth.* 142:127 (1992)) and (Apostolopoulos, V. et al., *Proc. Natl. Acad. Sci. USA*. 92:10128 (1995)). Stimulation of T-cell immunity has also been achieved by generating with galactose oxidase under experimental conditions, aldehydes in the galactosyl residues of cell-surface polysaccharides (Zeng, B., et al., *Science* 256:1560 (1992)). However, this immunostimulation was not reproducible (Rhodes, *J. Immunol. Today* 17:436 (1996)). These results highlight the problems associated with aldehyde instability and/or the inefficient production of aldehydes by enzymatic oxidation.

It is clinically and economically important for the vaccine industry to have new and effective adjuvants. The development of novel adjuvants that target antigen presenting cells and provide co-stimulatory signals to stimulate T-cell immunity is the subject of the present patent disclosure.

SUMMARY OF THE INVENTION

The present invention is directed to chemical conjugates (herein referred to as polysaccharide conjugates) that comprise (i) a polysaccharide capable of binding to the cell surface of Antigen Presenting Cells (APCs), and (ii) one or more molecules having a stable carbonyl group (i.e. an aldehyde or ketone group that is capable of reacting with amino groups to form an imine or Schiff base) wherein molecules (ii) are attached to the polysaccharide (i) through (iii) a direct covalent bond or covalently via a bifunctional linker in a manner that keeps the stable carbonyl group intact. The molecules having an imine-forming carbonyl group can be an aromatic or non-aromatic cyclic, aromatic or non-aromatic heterocyclic or non-cyclic compound. Preferably, aromatic or heteroaromatic ketones and aldehydes are employed as molecules (ii).

In a second aspect of the invention one or more molecules having a stable carbonyl group (i.e. an aldehyde or ketone group that is capable of reacting with amino groups to form an imine or Schiff base) are covalently attached, either directly or via a bifunctional linking molecule, to non-adjuvant carbohydrate antigens to provide intrinsic adjuvanticity to the non-adjuvant carbohydrate antigens. The conjugation of one or more molecules having a stable carbonyl group to said carbohydrate antigens results in a product having increased efficacy of preventive vaccinations compared to the non-conjugated carbohydrate antigens.

The present invention is directed to enhancing the potentiation of an immune response in a mammal, comprising administering an effective amount of a polysaccharide conjugate of the present invention to enhance the immune response of a mammal to one or more antigens.

The present invention is also directed to a method of vaccination, comprising administering one or more antigens, and a polysaccharide conjugate of the present invention.

The present invention is also directed to pharmaceutical and veterinary compositions comprising one or more of the polysaccharide conjugates of the present invention, and one or more pharmaceutically acceptable diluents, carriers or excipients. These compositions may be employed as immunopotentiators in animals and humans.

The present invention is also directed to vaccines comprising one or more antigens, and a polysaccharide conjugate of the present invention.

DETAILED DESCRIPTION OF THE PREFERRED EMBODIMENTS

The present invention is directed to polysaccharide conjugates, comprising:

(i) a polysaccharide capable of binding the surface of Antigen Presenting Cells (APCs); and (ii) one or more molecules having a stable carbonyl group (i.e. an aldehyde ketone group that is capable of reacting with amino groups to form an imine or Schiff base, also referred to as an "imine-forming compound");

wherein polysaccharide (i) is attached (iii) through a direct covalent bond, or covalently via the residue of a bifunctional linker to said one or more molecules (ii). The compounds having the imine-forming carbonyl group can be an aromatic or non-aromatic cyclic, aromatic or non-aromatic heterocyclic or non-cyclic compounds. Preferably, aromatic or heteroaromatic ketones and aldehydes are employed as (ii).

In order to more clearly explain this aspect of the present invention, polysaccharide conjugates can be represented by the Formula I:

$$P-(L-I)_x \qquad\qquad I$$

or pharmaceutically acceptable salts thereof, where

P is a polysaccharide that is capable of binding to the cell surface of an Antigen Presenting Cell;

each L is independently a covalent bond, or the residue of a bifunctional linking molecule;

each I is an imine-forming molecule. Preferred imine-forming molecules are residues of aromatic or heteroaromatic compounds having (a) a ketone or aldehyde functionality; and (b) a second functional group that is capable of reacting with a complementary functional group present on said polysaccharide or said bifunctional linking molecule, if present; and x is greater than or equal to one. The value of x will be determined by the number of reactive groups that are covalently modified on the polysaccharide. A number of factors and strategies will influence the value of x, as will be more fully detailed herein. Generally, x will be a function of the number of reactive hydroxyl, terminal end hemiacetal, carboxyl and/or amine groups that are present on the polysaccharide. Because of the diverse molecular weight distribution of useful polysaccharides (P), the degree of modification as expressed by x is expressed as the number of imine-forming groups introduced per hundred glycosyl residues. Using this convention, the value of x can vary from 1 to more than 100, with a preferred range of from 1 to about 50 imine-forming groups per 100 glycosyl residues.

The ratio of imine-forming molecules varies broadly depending upon the conjugation strategy employed. Control of this ratio is further described herein.

A free hydroxyl, terminal end hemiacetal, carboxylic acid or amine group of the polysaccharide is employed to covalently link the polysaccharide (P) to either (L) or (I). One or more of these reactive groups that are present on the polysaccharide can be first "activated" (as further described herein) to increase the reactivity of these groups, or the polysaccharide can be reacted with an imine-forming compound having an "activated" functional group.

An additional aspect of the invention is directed to conjugates comprising one or more compounds having a carbonyl group, wherein said compounds are covalently attached, either directly or via the residue of a bifunctional linking molecule, to non-adjuvant carbohydrate antigens to provide intrinsic adjuvanticity to the non-adjuvant carbohydrate antigens. The conjugation of an imine-forming molecules to said carbohydrate antigen results in a product having increased efficacy of preventive vaccinations compared to the carbohydrate antigen alone. Carbohydrate antigens include polysaccharides, including lipopolysaccharides and peptidoglycans from streptococci, staphylococci, and other bacteria that are used as vaccine antigens.

Polysaccharides

Polysaccharides that can be employed to form conjugates of the present invention include any polysaccharide, natural or chemically modified, that binds to cell surface receptors on APCs. For purposes of the present invention, useful polysaccharides comprise a minimum of two saccharides, preferably seven or more saccharides, and are unbranched or branched, and can have a molecular weight of from about 1000 to several million Daltons. Preferred polysaccharides have a molecular weight of from about 1,000 to about 500,000. The polysaccharides may possess chemical modifications as described herein.

The term "Antigen Presenting Cells" or the abbreviation "APCs" for purpose of the present invention mean dendritic cells and macrophages that are responsible for taking up antigens, processing them to small peptides, and expressing them on their surface in conjunction with class II MHC for presentation to T and B cells.

During evolution macrophages and dendritic cells have developed cell surface receptors that recognize the carbohydrate moieties from different microorganisms. These receptors play a critical role in phagocytosis as well as in pinocytosis, two processes that are involved in antigen presentation. Polysaccharides recognized by these cell-surface-receptors would be suitable for the construction of these adjuvants because such polysaccharides provide an effective mechanism for APC targeting. In some cases, carbohydrate sequences from bacterial, fungal, and animal origins are shared by plant polysaccharides. Thus, plant polysaccharides can provide a practical source of starting materials in some instances. Although these adjuvants can be prepared with either soluble or insoluble polysaccharides, the soluble forms are preferred.

The applications of the present disclosure are in no way limited to plant polysaccharides. They can be extended to other carbohydrate-containing compounds from different sources that are recognized by APCs surface receptors. Examples of these other polysaccharides are chitins and dextrans which are of animal and bacterial origin respectively. Examples of suitable carbohydrate-containing compounds are bacterial teichoic acids and their derivatives, bacterial lipopolysaccharides, lipid A, and their derivatives.

Finally, conjugation of compounds carrying imine-forming carbonyl groups to non-adjuvant carbohydrate-containing products is contemplated to be useful in providing intrinsic adjuvanticity to these products and to increase the efficacy of preventive immunizations. Examples of these products are polysaccharides from streptococci, staphylococci, and other bacteria that are used as vaccine antigens.

Among the preferred polysaccharides that are useful in the present invention are: β-glucans; mannans; pectins, and 2-acetamido glucans. Derivatives, including water-soluble derivatives, of these polysaccharides are also useful. See Provisional Appl. No. 60/083,106, and Divisional application. Ser. No. 09/165,310, fully incorporated by reference herein. Preferred polysaccharides are more fully described below.

β-Glucans: β-Glucans have a backbone chain of (1→3)-linked β-D-glucopyranosyl units which has β-D-glucopyranosyl units attached by (1→6) linkages. They are found in several sources, such as yeast, fungi, algae, and cereals. They have a broad range of molecular weights, i.e. between 5,000 to >500,000, which influence their immunomodulating properties. In general, β-glucans of high molecular weight that are relatively insoluble in water have higher biological activity. However, this lack of solubility has precluded the systemic administration of glucans. Modification of these polysaccharides by introduction of anionic groups, such as phosphate, sulfate, carboxyl, and others, has yielded soluble forms that apparently retain their biological activities. Soluble glucans can be prepared by one of the following procedures: i) isolation from yeast extracts (Hahn & Albersheim, 1978, *Plant Physiol*. 66:107), ii) sonication of glucan particles (Januz et al. 1986, *J Immunol*. 137:327, and iii) introduction of anionic groups to insoluble glucans by sulfonylation, phosphorylation, carboxymethylation, or sulfation ((Bohn & BrMiller, 1995, *Carbohydr. Polym.* 28:3), (Di Luzio, U.S. Pat. No. 4,739,046, 4/1988)). In β-glucans the only reducing glucosyl residue (linked at position 3) is located at the terminus of the backbone chain of (1→3)-linked β-D-glucosyl residues. The glucosyl residues attached by (1→6) linkages to the backbone chain do not have a free reducing group. The smallest fragment that binds to the monocyte glucan receptor is a (1→3)-linked β-glucanoheptasaccharide. However, this oligosaccharide does not have immunostimulating activity.

Mannans: Mannans are linear or branched polysaccharides formed exclusively of mannose. Mannans are found in plants, mold, bacteria and other organisms. In certain plants, linear mannans consist of β(1→4) linked mannosyl residues, whereas in some yeasts, the mannosyl residues are linked by α-(1→2) and α-(1→6) linkages. In the branched mannans from *Saccharomyces cerevisiae* (baker's yeast), the mannan consists of a α-(1→6) linked mannopyranosyl backbone structure substituted on the O-2 atoms by side-chains of α-D-mannopyranosyl, α-D-mannopyranosyl-α-(1→2)-α-D-mannopyranosyl and α-D-mannopyranosyl α-(1→3)-α-D-mannopyranosyl-α-(1→2)-α-D-mannopyranosyl. In addition, the *S. cerevisiae* mannan can also be phosphorylated (Barreto-Bergter and P. A. Gorin, *Adv. Carbohydr. Chem. Biochem.* 41:67 (1983), Vinogradov, E., et al., *Carbohydr. Res.* 307:177 (1998)). Although the ability of *S. cerevisiae* mannans to stimulate cell-mediated immunity is questionable, they enhance the action of lipopolysaccharides in stimulating T-cell responses (Ohta, M., et al., *Immunology* 60:503 (1987)). It appears that mannans can exert their immunostimulatory effects by binding to the macrophage mannose-binding cell-surface receptors. A derivative of β-mannans, the acetylated β-(1→4) polymannose, appears to stimulate the immune system in a manner similar to mannans.

Pectic polysaccharides: Several pectic polysaccharides are anti-complementary, and they may have different degrees of immunopotentiating activity (Yamada, H., et al., *Planta Medica* 56:182 (1990)). Oxidation of these polysaccharides with periodic acid results in a loss of anticomplementary activity on the classical pathway, but increased activity on the alternative pathway (Yamada, H. and Kiyohara, H., *Abstracts of Chinese Medicine* 3(1):104 (1989)). The polysaccharides showing some immunopotentiating activity and thus, being recognized by cell surface-receptors can be grouped broadly into homogalacturonans, rhamnogalacturonans, arabans, galactans, and arabinogalactans. However, not all of these compounds would have biological activity. In many cases, the activity would be dependent on structure, molecular weight, aggregation state, and other parameters. In general, pectic polysaccharides are a group of sugar polymers associated with 1,4-linked α-D-galactosyluronic acid residues. These polysaccharides may have several branched oligosaccharides linked to the backbone's galactosyluronic acid residues. From previous studies with saponins and other polysaccharides, branched oligosaccharides appear to be relevant for adjuvanticity.

2-Acetamido glucans: chitin, murein and their derivatives: Chitin is a linear N-acetyl-D-glucosamine (NAG) polymer linked by β(1→4) linkages that has about 16 percent of its NAG residues deacetylated. It is widely distributed in nature: it has been found in the exoskeleton of arthropods and in the cell walls of fungi. This polysaccharide has chains that form extensive intermolecular hydrogen bonds, making it insoluble in water and in different organic solvents. Removal of chitin's N-acetyl groups by strong alkali treatment yields chitosan, a β-(1→4) poly-D-glucosamine water-soluble polycation. Chitosan with 70% of its N-acetyl groups removed (deacetylated chitin), shows a significant immunostimulating activity (Azuma, I., *Vaccine* 10:1000 (1992)). To avoid the limitations imposed by its insolubility, several chitin derivatives that are more soluble in water have been developed, such as glycol chitin (Senzyu, K., et al., *J Japan, Agri. Chem. Soc.*, 23:432 (1950)) and carboxymethyl chitin that may also have immune stimulatory properties. Water-soluble alcohol-insoluble chitodextrins composed of heptamers or larger NAG oligosaccharides have been prepared by limited acid hydrolysis (Berger, L. R., et al., *Biochim. Biophys. Acta* 29:522 (1958)). Murein, the major component of bacterial cell walls, is a polysaccharide made of β-(1→4) linked NAG, with one of the NAG units substituted at C-3 with an O-lactic acid group by an ether linkage to yield N-acetyl-D-muramic acid (NAM) forming the repeating sequence NAG-NAM. Because of the lactic acid residues, isolated mureins are water-soluble. In the bacterial cell wall, murein is attached to certain peptides to form a cross-linked peptido-glycan. Because of their structural similarities, chitin and murein are recognized by the enzyme. lysozyme, and apparently also by receptors on the macrophage's cell surface. These structural similarities, which are also present in glycol chitin, may explain the immunostimulatory properties of chitin and some of its derivatives.

Molecules Having a Stable Carbonyl Group (Imine-Forming Molecules)

The second element of the conjugates of the present invention is one or more molecules having a stable carbonyl group (i.e. an aldehyde or ketone group) that is capable of reacting with amino groups to form an imine or Schiff base. The molecules having the imine-forming carbonyl group can be an aromatic or non-aromatic (saturated or partially unsaturated) carbocycle, aromatic or non-aromatic (saturated or partially unsaturated) heterocycle or a non-cyclic, aliphatic compound that may have one or more unsaturated bonds.

There is evidence that certain aromatic compounds with carbonyl groups are very effective in forming imines or Schiff bases upon reaction with amino groups on certain Th-cell surface receptor(s). Because carbonyl groups attached to aromatic compounds are more stable (whereas aliphatic aldehydes are generally unstable), their derivatives typically have a longer shelf life. Furthermore, the hydrophobic character of the cyclic compounds carrying the carbonyl groups will strengthen the interactions between cell surface receptors and the polysaccharide conjugates. Consequently, the compounds to be used to modify the polysaccharides are preferably aryl or heteroaryl aldehydes or ketones. To facilitate the access of these compounds to the amino groups on T-cells, it is more preferred that they also have some hydrophilic characteristics.

Compounds that embody some degree of all of the aforementioned properties are preferred agents for modifying the polysaccharides. Preferred compounds include mono- and di-substituted $C_{6-10}$ arylaldehydes and $C_{6-10}$ aryl($C_{1-4}$)alkylaldehydes, compounds comprising an aryl group, such as phenyl or naphthyl and include a formyl or formyl($C_{1-4}$)alkyl substituent. Preferably, these compounds further include one or two additional substituents such as halo, hydroxy, $C_{1-4}$ alkyl, $C_{1-4}$ hydroxyalkyl, $C_{1-4}$ alkoxy, trifluoromethyl, or benzyloxy. Suitable values include benzaldehyde and naphthaldehyde, substituted by one or two of hydroxy and halo. Examples include 2,3-, 2,4-2,5-, and 3,4-dihydroxybenzaldehyde, 5-chloro-2-hydroxybenzaldehyde, vanillin, ethyl vanillin, naringenin, 3- and 4-hydroxybenzaldehyde, and 4-hydroxyphenylacetaldehyde. A second preferred group is hydroxy substituted $C_{1-4}$alkyl ($C_{6-10}$)aryl ketones, such as 2-, 3-, and 4-hydroxyacetophenone, and hydroxy substituted aryl ketones such as 6-hydroxy-1,2-naphthoquinone. A third preferred group includes heteroaryl aldehydes and heteroaryl ketones. Useful heteroaryl groups are thiophene, furan, benzothiophene, benzofuran, pyridine, quinoline, pyridazine, pyrimidine, pyrazole, imidazole, 1,2,3-triazole, 1,2,4-triazole, isoxazole, and oxazole, each having a keto, formyl or formyl($C_{1-4}$) alkyl substituent, and preferably including an additional halo or hydroxy substituent, if these can be accommodated by available ring carbon atoms. Preferably, furanyl, pyridyl, and indolyl aldehydes and ketones are useful heteroaryl cores. Examples of useful heteroaryl aldehydes and ketones include pyridoxal, 2-thiophenecarboxaldehyde, and 3-thiophenecarboxaldehyde.

Another relatively stable group of cyclic compounds that contain imine-forming carbonyl groups are triterpenoids and steroids having a keto, formyl or formylalkyl substitution. Examples include androsterone, formyldienolone, progesterone, prednisolone, and other derivatives.

Bifunctional Linkers

Bifunctional linkers are well known in the art for various applications (Hermanson, G.T., *Bioconjugate Techniques*, Academic Press 1996). A number of bifunctional linkers can be employed to form an attachment between a suitable polysaccharide and a suitable imine-forming compound. "Residue of a bifunctional linker" refers to the structure that links a stable carbonyl compound to the polysaccharide after the terminal ends of the bifunctional linker have covalently bonded to said compound and said polysaccharide.

Non-limiting examples of linker groups that can be used to link the stable carbonyl containing compound to the polysaccharide are alkylene diamines ($NH_2$—$(CH_2)_n$—$NH_2$), where n is from 2 to 12; aminoalcohols (HO—$(CH_2)_r$—$NH_2$), where r is from 2 to 12; aminothiols (HS—$(CH_2)_r$—$NH_2$), where r is from 2 to 12; and amino acids that are optionally carboxy-protected; ethylene and polyethylene glycols (H—(O—$CH_2$—$CH_2$)$_n$—OH, where n is 1–4). Suitable bifunctional diamine compounds include ethylenediamine, 1,3-propanediamine, 1,4-butanediamine, spermidine, 2,4-diaminobutyric acid, lysine, 3,3'-diaminodipropylamine, diaminopropionic acid, N-(2-aminoethyl)-1,3-propanediamine, 2-(4-aminophenyl)ethylamine, and similar compounds.

When a carboxyl group of the polysaccharide is employed as the conjugating group, one or more amino acids can be employed as the bifunctional linker molecule. Thus, an amino acid such as β-alanine or γ-aminobutyric acid, or an oligopeptide, such as di- or tri- alanine can be employed as a suitable linking molecule.

Preferred bifunctional linking groups include:
  —NH—$(CH_2)_r$—NH—, where r is from 2–5,
  —O—$(CH_2)_r$—NH—, where r is from 2–5,
  —NH—$CH_2$—C(O)—,
  —O—$CH_2$—$CH_2$—O—$CH_2$—$CH_2$—O—,
  —NH—NH—C(O)—$CH_2$—,
  —NH—$C(CH_3)_2$—C(O)—,
  —S—$(CH_2)_r$—C(O)—, where r is from 1–5,
  —S—$(CH_2)_r$—NH—, where r is from 2–5,
  —S—$(CH_2)_r$—O—, where r is from 1–5,
  —S—$(CH_2)$—$CH(NH_2)$—C(O)—,
  —S—$(CH_2)$—CH(COOH)—NH—,
  —O—$CH_2$—CH(OH)—$CH_2$—S—$CH(CO_2H)$—NH—,
  —O—$CH_2$—CH(OH)—$CH_2$—S—$CH(NH_2)$—C(O)—,
  —O—$CH_2$—CH(OH)—$CH_2$—S—$CH_2$—$CH_2$—NH—,
  —S—$CH_2$—C(O)—NH—$CH_2$—$CH_2$—NH—, and
  —NH—O—C(O)—$CH_2$—$CH_2$—O—$P(O_2H)$—.

The preferred combinations of polysaccharide, imine-forming compound, linkers and ratios for each may include but are not limited to:

| Polysaccharide (P) | imine-forming compounds (I) | linker (L) | L/P* | I/P* |
|---|---|---|---|---|
| Glucans | 4-hydroxybenzaldehyde | —NH—$(CH_2)_n$—NH—C(O)— | 5-30 | 5-20 |
| Glucans | 4,6-dioxoheptanoic acid | —C(O)—NH—$(CH_2)_n$—NH— | 5-30 | 5-20 |
| Glucans | pyridoxal 5-phosphate | —NH—O—C(O)—$(CH_2)$—C—O— | 5-30 | 5-20 |
| Glucans | 2,4-dihydroxybenzaldehyde | —NH—$(CH_2)_n$—NH—C(O)— | 5-30 | 5-20 |
| Glucans | pyridoxal 5-phosphate | —NH—$(CH_2)_n$—NH—C(O)— | 5-30 | 5-20 |
| Glucans | 2-thiophenecarboxaldehyde | —C(O)—NH—$(CH_2)_n$—NH— | 5-30 | 5-20 |
| Glucans | 3-thiophenecarboxaldehyde | —NH—O—C(O)—$(CH_2)$—C—O— | 5-30 | 5-20 |
| Mannans | 4-hydroxybenzaldehyde | —NH—$(CH_2)_n$—NH—C(O)— | 5-30 | 5-20 |
| Mannans | 4,6-dioxoheptanoic acid | —C(O)—NH—$(CH_2)_n$—NH— | 5-30 | 5-20 |
| Mannans | pyridoxal 5-phosphate | —NH—O—C(O)—$(CH_2)$—C—O— | 5-30 | 5-20 |
| Mannans | 2,4-dihydroxybenzaldehyde | —NH—$(CH_2)_n$—NH—C(O)— | 5-30 | 5-20 |
| Mannans | pyridoxal 5-phosphate | —NH—$(CH_2)_n$—NH—C(O)— | 5-30 | 5-20 |
| Mannans | 2-thiophenecarboxaldehyde | —C(O)—NH—$(CH_2)_n$—NH— | 5-30 | 5-20 |
| Mannans | 3-thiophenecarboxaldehyde | —NH—O—C(O)—$(CH_2)$—C—O— | 5-30 | 5-20 |
| Pectic Polysaccharides | 4-hydroxybenzaldehyde | —NH—$(CH_2)_n$—NH—(O)— | | |
| Pectic Polysaccharides | pyridoxal 5-phosphate | —NH—$(CH_2)_n$—NH—C(O)— | 5-30 | 5-20 |
| Pectic Polysaccharides | 2-thiophenecarboxaldehyde | —C(O)—NH—$(CH_2)_n$—NH— | 5-30 | 5-20 |
| Pectic Polysaccharides | 3-thiophenecarboxaldehyde | —NH—O—C(O)—$(CH_2)$—C—O— | 5-30 | 5-20 |
| Murein | 4-hydroxybenzaldehyde | —$CH_2$—CHOH—$(CH_2)$—O—$(CH_2)_n$—O—$CH_2$—CHOH—$CH_2$— | 5-30 | 5-20 |
| Murein | 4,6-dioxoheptanoic acid | —C(O)—$(CH_2)_n$—NH— | 5-30 | 5-20 |
| Murein | 2,4-dihydroxybenzaldehyde | —$CH_2$—CHOH—$CH_2$— | 5-30 | 5-20 |
| Murein | pyridoxal 5-phosphate | —NH—$(CH_2)_n$—NH—C(O)— | 5-30 | 5-20 |
| Murein | 2-thiophenecarboxaldehyde | —C(O)—NH—$(CH_2)_n$—NH— | 5-30 | 5-20 |
| Murein | 3-thiophenecarboxaldehyde | —NH—O—C(O)—$(CH_2)$—C—O— | 5-30 | 5-20 |
| Glycol chitin | pyridoxal 5-phosphate | —O—C(O)—$(CH_2)_n$—C—O— | 5-30 | 5-20 |
| Glycol chitin | pyridoxal 5-phosphate | —NH—$(CH_2)_n$—NH—C(O)— | 5-30 | 5-20 |
| Glycol chitin | 2-thiophenecarboxaldehyde | —C(O)—NH—$(CH_2)_n$—NH— | 5-30 | 5-20 |
| Glycol chitin | 3-thiophenecarboxaldehyde | —NH—O—C(O)—$(CH_2)$—C—(O)— | 5-30 | 5-20 |

*I/P and L/P ratios are expressed as I or L molecules incorporated per 100 carbohydrate residues n = 1 to 8

Preparation of Imine-forming Polysaccharide Adjuvants

The present invention is also directed to processes for the preparation of polysaccharide conjugates of the present invention. Structure/function studies of adjuvant polysaccharides and saponins, have shown that the integrity of the carbohydrate chains' structures are critical for their adjuvanticity. Apparently, the recognition of the carbohydrate moieties by APCs surface-receptors is essential for targeting of the cells as well as to exert their immunostimulatory effects. The adjuvant activity of triterpene saponins also requires an aldehyde group in the triterpenoid moiety. It has also been recently shown that small organic molecules capable of forming imines or Schiff-bases can provide a co-stimulatory signal to T-cells, thus obviating the need for their stimulation by the B7-1 receptor present on APCs (Rhodes, J., et al., *Nature* 377:71 (1995)). Addition of (i) a cyclic or heterocyclic aromatic compound, or cyclic compounds having imine-forming carbonyl groups, to (ii) certain polysaccharides recognized and bound by APCs will result in products with superior adjuvant properties. These adjuvant molecules will possess immunomodulating and targeting properties.

A. Addition of Imine-forming Compounds to Terminal Reducing Glycosyl Residues

A method for covalently attaching imine-forming compounds to terminal reducing glycosyl residues of β-glucans and β-mannans is described herein with reference to Scheme 1.

SCHEME 1
Addition of imine-forming compounds to β–glucans via terminal-end hemiacetal

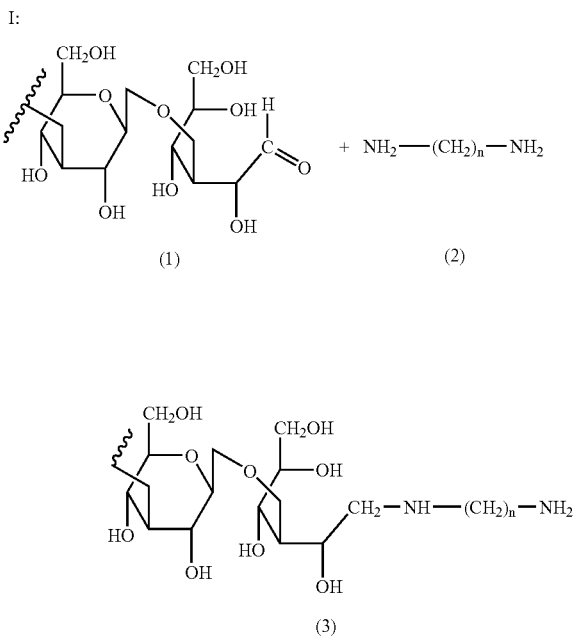

-continued

II:

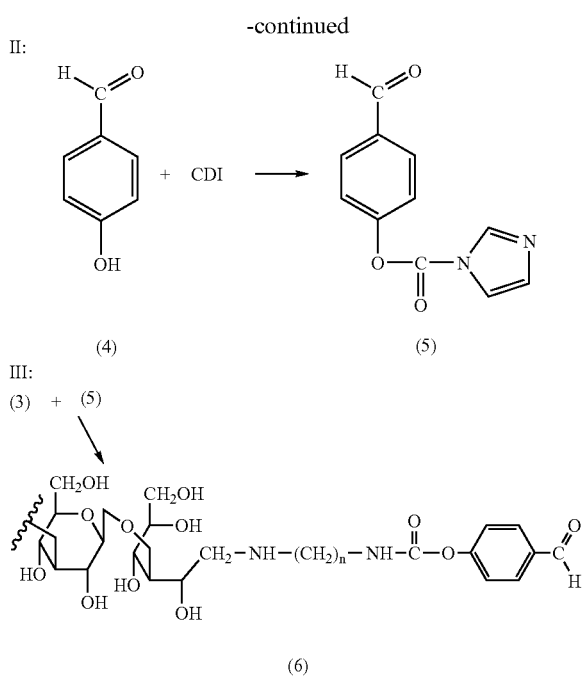

(4)    (5)

III:

(3) + (5)

(6)

Because β-glucans and β-mannans are comprised of either glucosyl or mannosyl residues, the functional groups available for chemical modifications are largely hydroxyl groups (—OH) with limited reactivity. In addition, there is one terminal reducing glucosyl residue per polymer chain. In general the primary hydroxyl groups of glycosyl residues are more reactive than the secondary hydroxyl groups. However, it is possible that the structure of a particular polysaccharide may impose certain constraints (steric or electronic) on the hydroxy groups' reactivity. This will create a hierarchy of hydroxy groups that could favor the production of certain dominant products under limiting reaction conditions.

The restricted number of terminal reducing sugars in glucans and mannans provides a highly specific site for introduction of new chemical groups. This specificity makes the terminal-end glycosyl hemiacetals a preferred group for commercial production of modified polysaccharide adjuvants of the present invention.

The chemical modifications described here can be used with soluble or insoluble glucans from different organisms. However, they are provided only as examples, not as limitations of the synthetic procedures available. Because the carbohydrate moieties' role in these new adjuvants is the targeting of APCs, the useful molecular weight range can be very broad, i.e. from about a thousand to several millions. In the present invention, soluble oligo- and polysaccharides of molecular weights ranging from about 1,000 to several hundred thousands are preferred.

The reducing terminus of oligosaccharides provides a selective and convenient site for the direct covalent attachment of molecules with amino groups, such as bifunctional diamine compounds. The reductive amination procedure involves reacting the terminal reducing glycosyl residue(s) in the oligosaccharide (or polysaccharide) with a compound carrying one or more primary amino groups in the presence of sodium cyanoborohydride (NaCNBH$_3$). The cyanoborohydride anion selectively reduces the imine or Schiff base formed by an aldehyde or ketone and an amine. Since only a small percentage of the time the terminal glucosyl hemiacetals are in their formyl or open form, the reaction may proceed at very low rate. Because the presence of both imine-forming carbonyls and primary amines in a molecule would largely result in the production of undesirable products, the additions are carried on in a two-step procedure, summarized as follows:

Step 1. Glucan/mannan oligosaccharides or polysaccharides (1) are suspended/dissolved in an appropriate solvent, such as aqueous acetonitrile, dimethylformamide (DMF), pyridine, or aqueous buffers containing a tertiary amine buffer pH 9.0, and a suitable diamine compound (2), where n is from about 2 to about 12, preferably, 2 to 4 is added in the same solvent with the pH adjusted to 9.0. [Suitable bifunctional diamine compounds are ethylenediamine, 1,4-butanediamine, spermidine, 2,4-diaminobutyric acid, lysine, 3,3'-diaminodipropylamine, diaminopropionic acid, N-(2-aminoethyl)-1,3-propanediamine, 2-(4-aminophenyl)ethylamine, and similar compounds]. The diamine compound that is added should be about 5 to 10-fold excess compared to the molar equivalent of free aldehyde groups in the carbohydrate (i.e. one free aldehyde per carbohydrate polymer chain). Sodium cyanoborohydride dissolved in 50% acetonitrile is added to the reaction mixture, and the reaction is allowed to proceed at 25° C. with gentle stirring for several days. The amount of amine compound incorporated in the polysaccharide depends on the reaction conditions as well as the glucan preparation. Therefore, the amount of diamine compound incorporated is determined daily to establish the reaction time needed to reach the required level of diamine incorporation. The modified aminated glucan/mannan (3), containing 1 mole of diamine spacer per polysaccharide chain) is recovered by precipitation with 6 volumes of ethanol, or other suitable solvent, for 8 hours at 4° C. The precipitate is redissolved in water, is filtered, and is re-precipitated with 5 volumes of ethanol for 24 hours at 4° C. The material is dissolved in water and is lyophilized.

Step 2. Aromatic cyclic or heterocyclic compounds with an imine-forming carbonyl group (4), and one or more hydroxyl groups, such as 4-hydroxybenzaldehyde, 2,4-dihydroxybenzaldehyde, vanillin, ethyl vanillin, naringenin, and other similar compounds are preferred for addition to the aminated polysaccharides. However, other compounds having carbonyl groups such as steroid and triterpenoid derivatives can also be used. Small aliquots 10 mmol of either 4-hydroxybenzaldehyde (1.2 g), vanillin (1.5 g), or 5-chloro-2-hydroxybenzaldehyde (1.6 g) dissolved in 10 ml of dioxane or acetone are added to 10 mmol (1.6 g) of 1,1'-carbonyldiimidazole (carbodiimidazole or CDI) or N,N'-carbonyldiimidazole dissolved in 10 ml of anhydrous dioxane or acetone. The mixture is reacted for 6–8 hours at room temperature with mixing while protected from atmospheric moisture. The reaction products are a highly reactive intermediate imidazole carbamate (5) which is formed with the hydroxy from the aromatic aldehyde derivatives, plus imidazole.

Step 3. This reaction mixture can be added to the aminated polysaccharides without prior isolation of the intermediate imidazole carbamate. The carbamate couples with the modified polysaccharides' amino groups to yield stable carbamate linkages. (Imidazole carbarnate derivatives can be isolated by chromatography, differential extractions, or other procedures). To minimize reactions of the polysaccharides' hydroxy groups with the imidazole carbamate intermediate, the coupling reaction should take place in the presence of equimolar amounts of amino and imidazole carbamate groups. The amount of amino groups in the aminated polysaccharide is determined with trinitrobenzenesulfonic acid (TNBS), or is estimated from its content of C, N, H, and O as determined by elementary analysis. The aminated glucan or mannan is suspended in a suitable anhydrous organic solvent, such as DMF, dioxane, or pyridine, and the pH is adjusted to about 9.5–10 with triethylamine. An aliquot of the carbamate intermediate containing an amount equivalent to the amino groups of the polysaccharide preparation is added, and the reaction is allowed to proceed for 12 to 18 hours at room temperature protected from moisture. About 6–8 volumes of cold ethanol are added to the reaction to precipitate the polysaccharide-aromatic aldehyde conjugate (6), which is collected by filtration. The conjugated polysaccharide is redissolved in water, and re-precipitated again with 6–8 volumes of ethanol or other suitable solvent. Efficacy of coupling is determined by one of the following methods: i) measuring the residual amino groups in the preparation with TNBS, ii) determining spectrophotometrically the amount of aromatic compound present in the preparation, or iii) by direct estimation of the aldehyde groups either with Schiff reagent or spectrophotometrically with N-methyl benzothiazolone hydrazone (MBTH) (Paz, M. A., et al., *Archiv. Biochem. Biophys.* 109:548 (1965)).

The polysaccharide-aromatic aldehyde conjugate is dissolved in water and is lyophilized.

It is also possible to create new aldehyde groups in the polysaccharide chain by mild oxidation with periodic acid. After oxidation, the polysaccharide with the additional aldehyde groups is precipitated with alcohol and subjected to reductive amination as described above.

B. Addition of Imine-forming Compounds Via the Polysaccharide's Hydroxy Groups

Another method to prepare glucan or mannan conjugated to carbonyl carrying compounds is to use the polysaccharides hydroxy groups for conjugate formation. This method is illustrated by reference to Scheme 2. Because of the number of hydroxy groups per glycosyl residue, this method allows the preparation of conjugates with higher densities of carbonyl groups. One can activate the polysaccharide's hydroxy groups and let react with the carbonyl-carrying molecule.

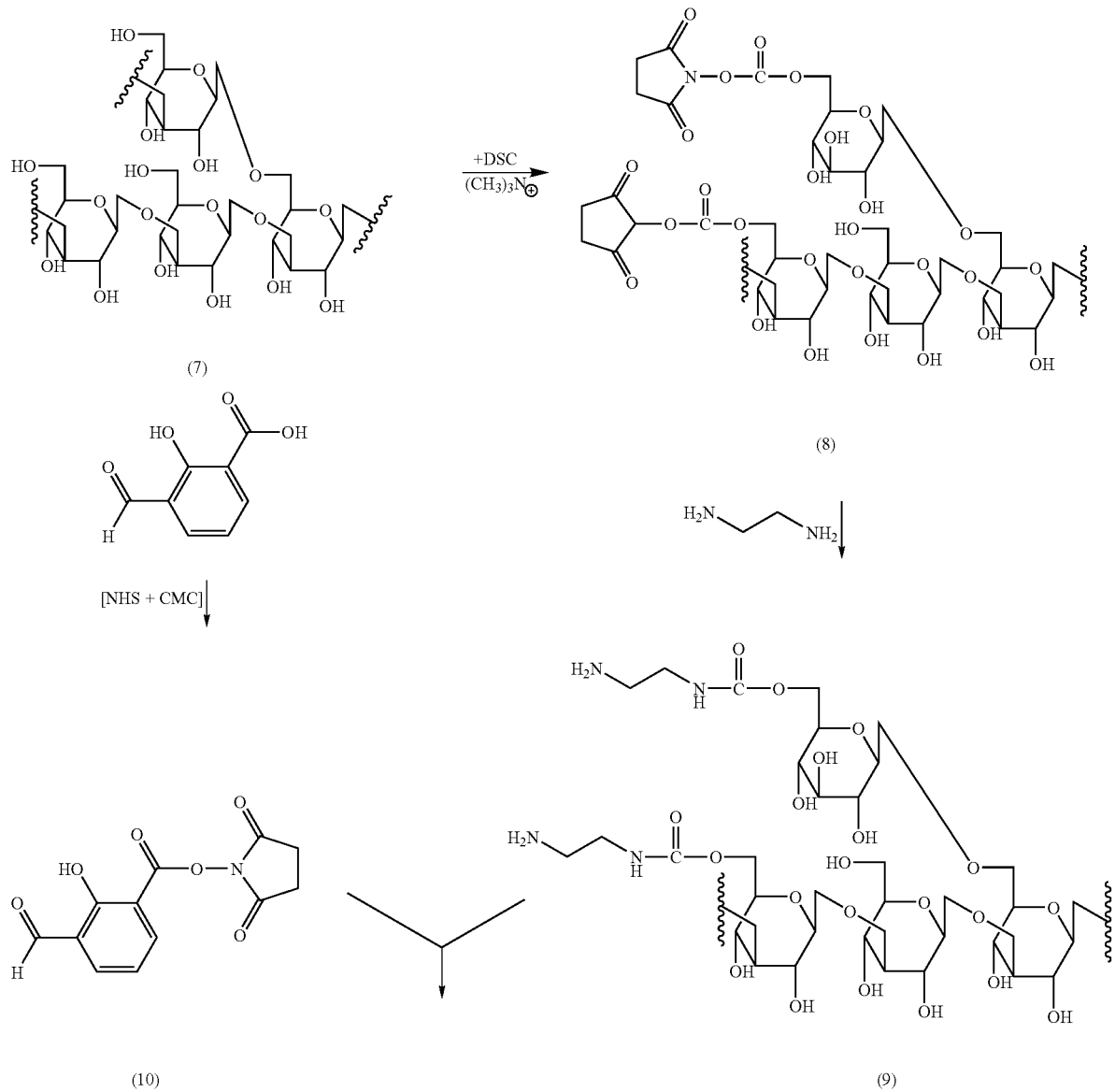

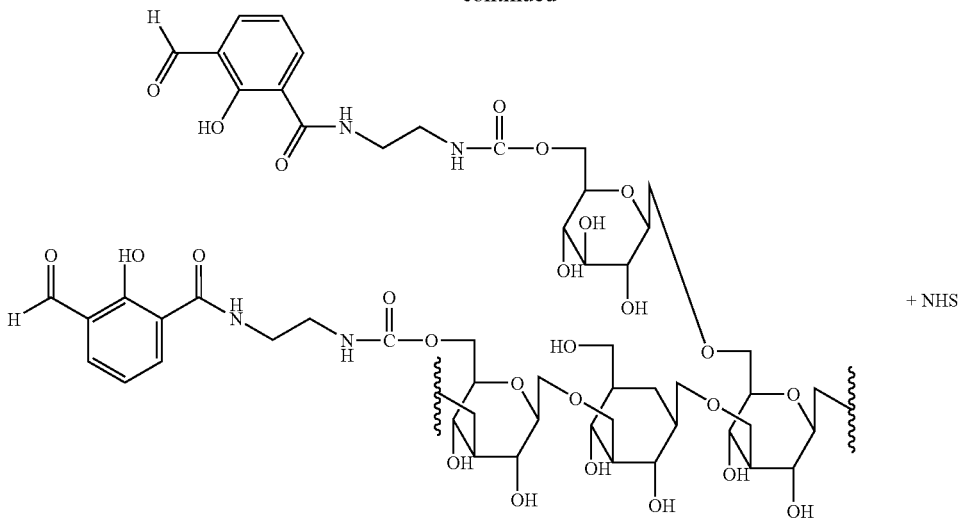

(11)

Conjugation of compounds carrying carbonyl groups to the hydroxyl groups of polysaccharides can be made with N,N'-disuccinimidyl carbonate (DSC). Hydroxyl groups that are activated with DSC react almost exclusively with primary amines, avoiding the cross-linking of the polysaccharide chains via their -OH groups. Hydroxyl groups of β-1,3 glucans are activated with DSC, and subsequently reacted with ethylenediamine to introduce amino groups into the glucan. These amino groups can then react with one of the following N-hydroxysuccinimide (NHS) esters: 3- or 5-formylsalicylic acid-, 4-formylcinnamic acid, and 3- or 4-carboxybenzaldehyde, to form an aromatic aldehyde-glucan conjugate. Scleroglucan (7), a β-1,3 glucan with single β-1,6 linked D-glucose branches on every third glucose unit and with a molecular weight of about 130,000, is dissolved in water (2–5% solution), and lyophilized to yield a powdery product easily suspended in organic solvents. Two g of the lyophilized scleroglucan (12 mmoles glucosyl residues) are suspended in 40 ml of DMF containing 0.8 g of DSC (3 mmoles). To this suspension add in an hour 20 ml of dry pyridine containing 0.75 ml of anhydrous triethylamine (5.5 mmoles) and let react for an additional 4 hours at room temperature. One volume of acetone is added to this reaction, and the insoluble activated scleroglucan succinimidyl carbonate (8) is collected and rinsed by filtration. The activated scleroglucan, dissolved or suspended in 20 ml of water, is slowly added with stirring to 100 ml of 0.2 M K potassium bicarbonate containing 2 ml of ethylenediamine (30 mmoles or 10× excess over the maximum polysaccharides' activated —OH groups) and adjusted to pH 8.5. After 4 hours at room temperature, the reaction is concentrated and dialyzed against water to remove excess of reactants from the aminated scleroglucan derivative (9) and lyophilized. The aminated polysaccharide is then reacted with succinimidyl-3-formylsalicylic acid ester.

Succinimidyl-3-formylsalicylic acid ester is prepared as follows: to 0.49 g of 3-formylsalicylic acid (3 mmoles) and 0.42 g of NHS (3.5 mmoles) dissolved in 10–15 ml of DMF, 1.28 g of CMC or 1-cyclohexyl-3-(2-morpholinoethyl) carbodiimide p-toluenesulfonate (3 mmoles) are added and left to react for 5 hours at room temperature protected from moisture. To this reaction mixture add 2.1 ml of 2-mercaptoethanol (30 mmoles) to quench the unreacted CMC, mix and react for 10 minutes at room temperature and use the succinimidyl-3-formylsalicylic acid ester (10) immediately. (The 3-formylsalicylic acid can be replaced by an equimolar amount of 5-formylsalicylic acid, 4-formylphenoxyacetic acid or 3-carboxybenzaldehyde.)

To the aminated scleroglucan (about 2 g) dissolved in 25 ml of 0.1 M of MOBS (4-[N-morpholino]butanesulfonic acid) buffer, pH 7.6, add with stirring the DMF containing the succinimidyl 3-formylsalicylic acid ester and the mercaptoethanol, and let react with stirring at room temperature for 4–6 hours. The 3-formylsalicylic acid-scieroglucan derivative (11) is precipitated with 6–8 volumes of ethanol, and collected and washed with ethanol to remove excess of reactants. The precipitated scleroglucan derivative is dissolved in 50 ml of water, dialyzed against water, and lyophilized. The 3-formylsalicylic acid content of the scleroglucan derivative can be determined from its H, C, N, and O elementary composition. The content of aromatic aldehyde residues in the scleroglucan derivative can also be determined spectrophotometrically as follows: dissolve 5–8 mg of the scleroglucan derivative in 4 ml of 0.05 M KOH and read the UV spectra between 220 and 320 nm using as a blank a solution of equal concentration of unmodified scleroglucan in 0.05 M KOH. Calculate the 3-formylsalicylic acid incorporated using the extinction coefficient for this compound determined in 0.05 M KOH. The aldehyde content can also be determined either colorimetrically with Schiff reagent or spectrophotometrically with MBTH.

Conjugation of compounds carrying both carbonyl and hydroxyl groups to polysaccharides, such as mannans, can be carried out by activating the polysaccharide hydroxyl groups with p-toluenesulfonyl (tosyl) chloride (Nilsson, K., et al., *Acta Chem. Scan*. 35:19 (1981); Nilsson, K., et al., *Methods Enzymol*. 104:56–69 (1984)). See Scheme 3-a.

SCHEME 3-A
Addition of imine-forming compounds to mannan
I
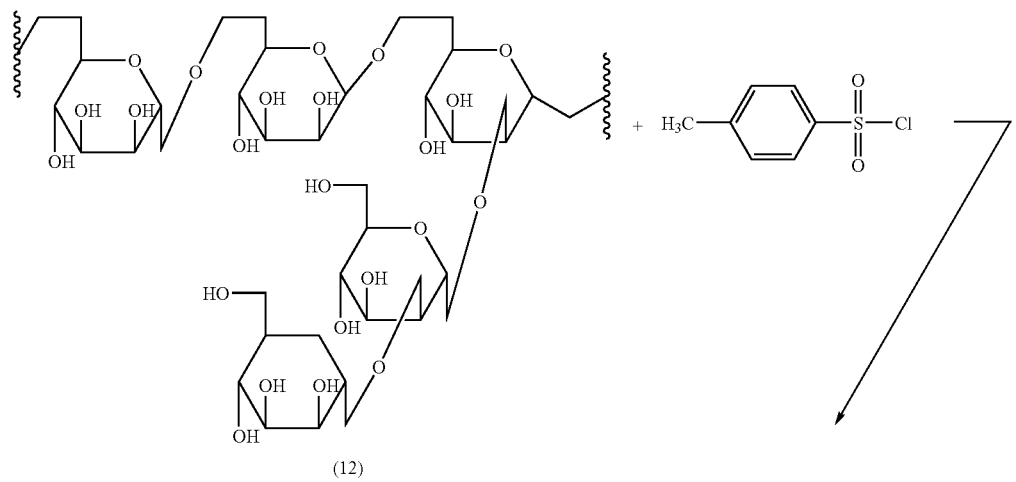
II
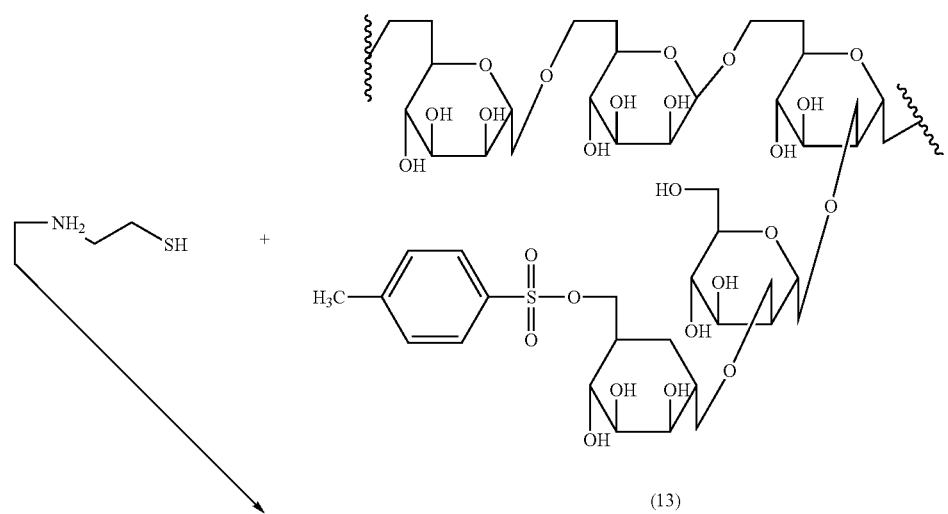
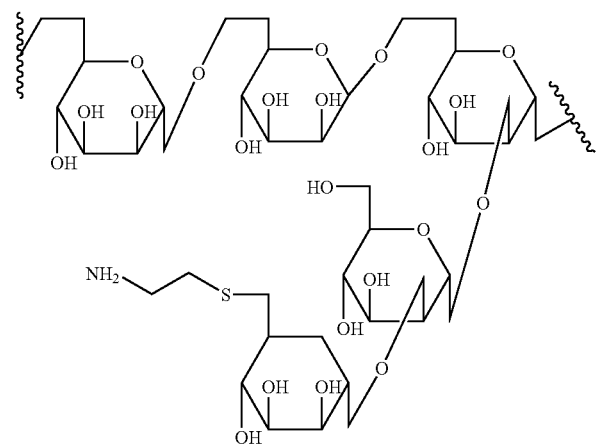

Because several of the primary hydroxyl groups in mannan from *S. cerevisiae* are either phosphorylated or linked to phosphoesters, and are unavailable for tosylation, it is necessary to remove the phosphate by alkaline hydrolysis under reducing conditions. Baker's yeast mannan, 4–5 g, is dissolved in 200 ml of 1.5 M KOH containing 1% sodium borohydride and refluxed at 100° C. for 2 hours with constant stirring. After 2 hours at 100° C. cool the solution to about 50° C. and neutralize it with about 18 ml of acetic acid. The neutralized mannan solution is added with stirring to 1.5 liters of chilled ethanol and the mixture is left standing for 4 hours to precipitate the mannan. The precipitated mannan is collected by filtration, dissolved in water, dialyzed against water to remove salts and lyophilized.

One g of lyophilized mannan (12) (~6 mmoles mannose), dried by suspension in pyridine and the azeotrope removed, is resuspended in 15 ml of DMF, and mixed with 2.5 g of tosyl chloride (2.15 mmoles) dissolved in 5 ml of DMF. To this mixture add 5 ml of pyridine and react with stirring for 18 hours at room temperature, to yield a tosylated mannan (13) having 1 tosyl group for every 20–25 mannosyl residues. The degree of tosylation is determined in a sample of the activated mannan that has been precipitated and washed with alcohol as follows. Dissolve 8 mg of the precipitated mannan in 4 ml of 0.1 N KOH, and measure its UV absorption spectra (220 to 360 nm) against a blank of unmodified mannan (8 mg in 4 ml of 0.1 N KOH). Determine the content of tosyl groups by using an extinction coefficient for tosyl of 480 $M^{-1}cm^{-1}$ at 261 nm. To the tosylated mannan (13) preparation (~0.9 g) resuspended in 20 ml of 0.5 M K bicarbonate, add 2 g of 2-cysteamine HCl (18 mmoles) and adjust the pH with 1 N KOH to 9.5–10. Let react for 24 hours at 40° C. with stirring and under a nitrogen atmosphere to introduce about 1 cysteamine residue per tosylated —OH. Dialyze the reactions against water to remove excess of reactants and salts, and lyophilize the mannan-cysteamine derivative (14). The amount of cysteamine bound to the tosylated mannan can be determined from the derivative's H, C, S, O and N elementary composition. The cysteamine incorporation can also be estimated by mixing 10 ml of 0.05 M K carbonate buffer pH 9.5 containing 2 mg of the aminated mannan with 1 ml of an aqueous TNBS (7.2 mg/ml) and reacting for 2 hours at 40° C. Measure the absorbancy at 363 nm against a blank of buffer plus TNBS, and determine the incorporated —$NH_2$ using a molar extinction coefficient of 11,000 $M^{-1}cm^{-1}$.

SCHEME 3-B
Addition of imine-forming compounds to mannan

III

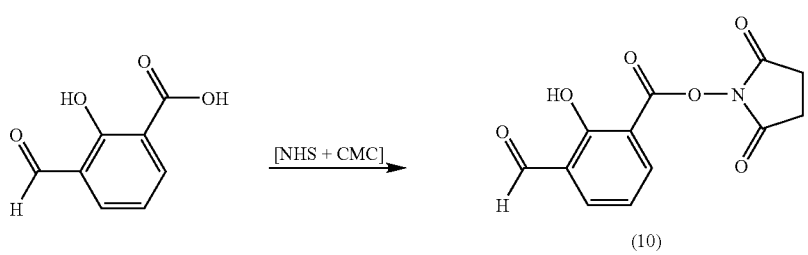

(10)

IV

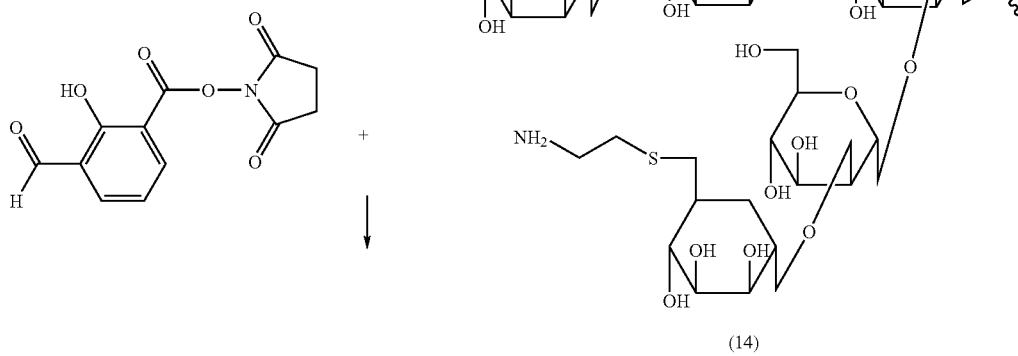

(14)

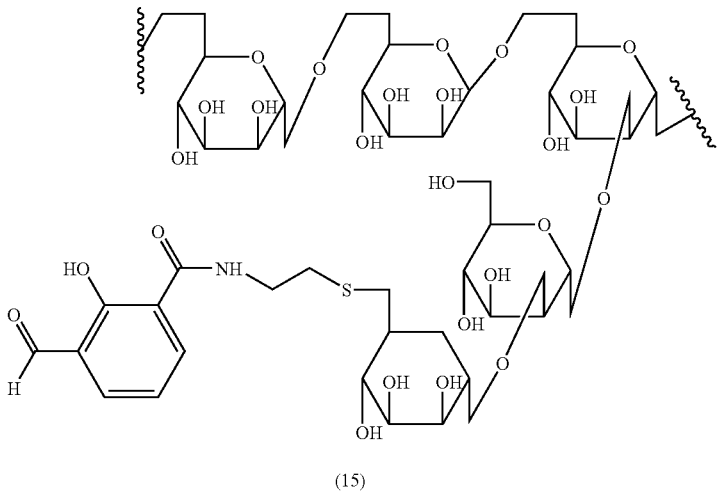

(15)

Scheme 3-b illustrates attachment of an imine-forming compound to mannan-cysteamine. Suspend the lyophilized mannan-cysteamine (0.8–0.9 g) in 20 ml of pyridine, remove the azeotrope under reduced pressure to eliminate water, and resuspend the mannan-cysteamine residue (14) in 40 ml of pyridine:tetrahydrofuran (10:1). To this suspension add 0.37 g of DCC (dicyclohexylcarbodiimide) (1.8 mmole), 0.3 g of p-carboxybenzaldehyde and 0.21 g of NHS (1.8 mmole) to form in situ the p-carboxybenzaldehyde-NHS ester intermediate (10). Let the reaction proceed for 24 hours with stirring at room temperature. Stop the reaction by adding 100 ml of water to the mixture to accelerate the formation of DCU. After 30 minutes, add an additional 400 ml of water to dissolve the p-carboxybenzaldehyde-mannan derivative (15). After 6 hours of stirring at room temperature, let the dicyclohexyl urea (DCU) settle overnight and remove it by decantation. Filter the supernatant, concentrate it under reduced pressure, dialyze against water and lyophilize the p-carboxybenzaldehyde-mannan derivative (15). The aromatic aldehyde incorporated to the mannan can be determined spectrophotometrically as follows. Dissolve 5–8 mg of the mannan derivative in 4 ml of 0.05 M KOH and read the UV spectra between 220 and 320 nm using as a blank a solution of equal concentration of unmodified mannan in 0.05 M KOH. To calculate the p-carboxybenzaldehyde concentration use its extinction coefficient determined in 0.05 M KOH. The aldehyde content can also be determined either calorimetrically with Schiff reagent or spectrophotometrically with MBTH.

C. Addition of Imine-forming Compounds to Carboxy Groups of Pectic Polysaccharides Carboxylic groups from pectic polysaccharides, (homogalacturonans, rhamnogalacturonans, arabinogalactans, arabans, or galactans), such as galacturonic, glucuronic, aceric, Kdo or 3-deoxy-D-manno-octulosonic acid, and other acids, are reactive groups that can be used to couple the pectins to carbonyl carrying (imine-forming) compounds. Carboxylic groups can be coupled specifically to amines by using dicyclohexylcarbodiimide (DCC) and N-hydroxysuccinimide (NHS). See Scheme 4.

SCHEME 4
Addition of imine-forming compounds to pectic polysaccharides

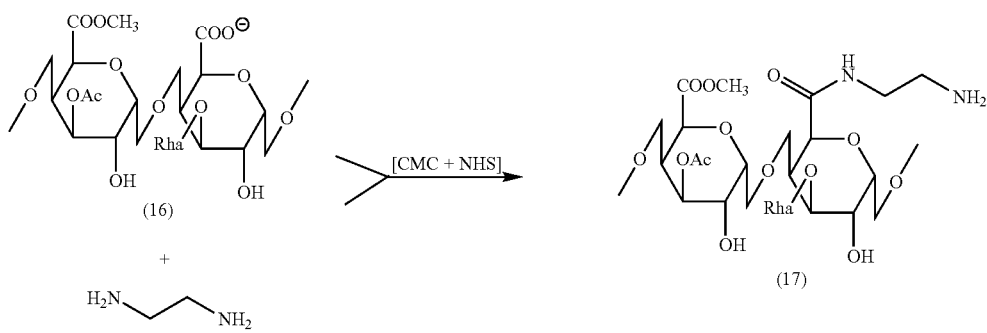

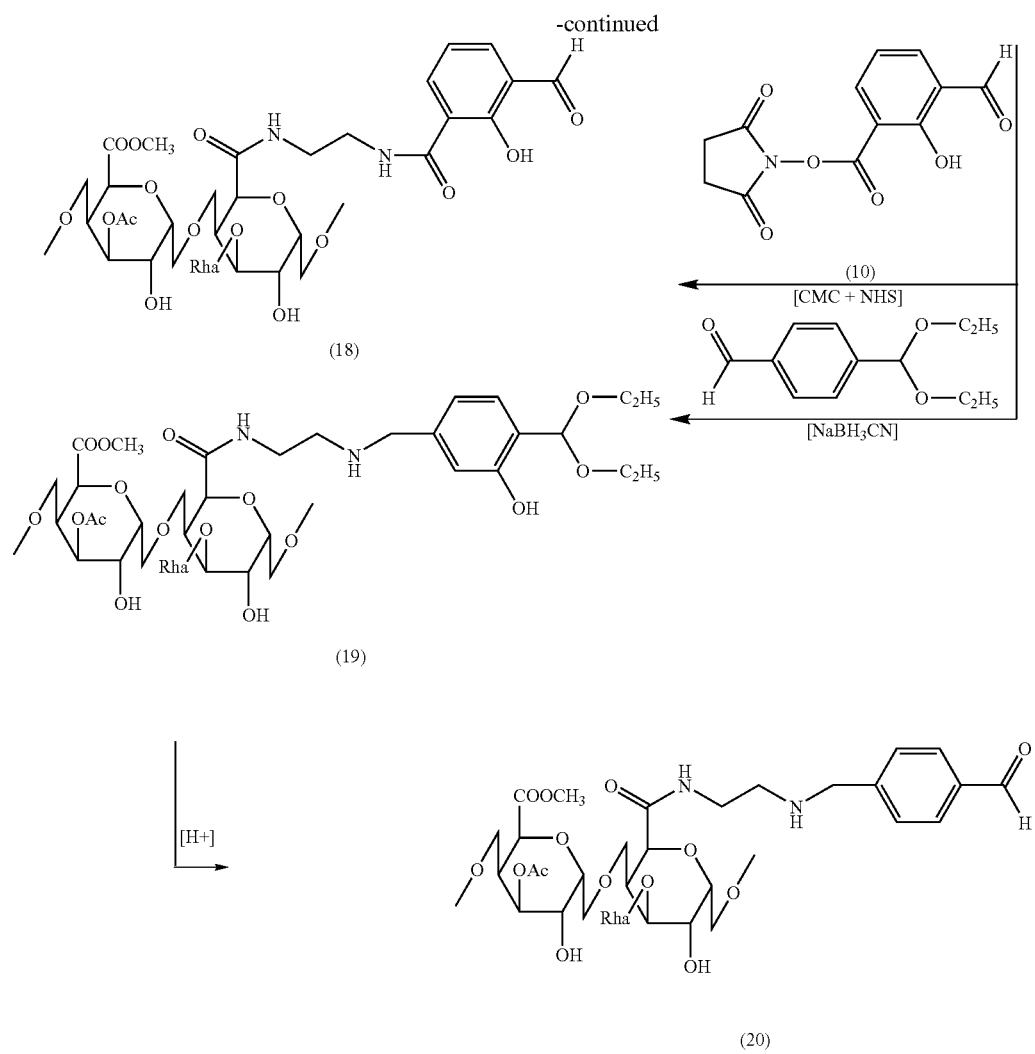

This reaction can be carried out in organic solvents such as dioxane, DMF, pyridine, acetonitrile, or mixtures of the same. The coupling reaction can also be carried out in aqueous or semi-aqueous media using one of the water-soluble carbodiimides such as 1-ethyl-3-(3-dimethylamino-propyl)carbodiimide (EDC) or CMC, in conjunction with either N-hydroxysulfosuccinimide (sulfo-NHS) or NHS. The number of amine groups per glycosyl residue can be selected by use of a limiting amount of CMC in the presence of an excess of diamine ligand. This approach is illustrated in Scheme 4. In one example, to 2.0–2.2 g of low methoxyl $Na^+$ pectinate (<11 mmoles galacturonic acid) dissolved in 50 ml of hot water, 15 ml of settled strong cation-exchanger polystyrene sulfonic acid resin in $H^+$ form (Dowex, 50-X8) are added and stirred for 2 hours. The suspension is filtered to remove the resin, and the resin is washed with 20 ml of warm water. The pectin ($H^+$ form) (16) solution is reduced in volume by partial lyophilization, low-pressure rotary evaporation, or reverse osmosis, to approximately 40 ml. To the pectin solution ($H^+$ form) add pyridine to bring the pH to ~7.6. To this solution 1 g of CMC (2.35 mmoles) and 0.41 g of NHS (3.4 mmoles) dissolved in 10 ml of pyridine and 2 ml of ethylenediamine (30 mmoles) are added with stirring, and the mixture is left to react overnight at room temperature with constant stirring. Separation of the aminated polysaccharide (17) from the other reactants is accomplished by precipitating it with 6–8 volumes of ethanol. The ethanol-washed, precipitated, aminated pectin is dissolved in water, dialyzed and lyophilized to yield a powdery product easily dissolved in water, and its amino group content determined with TNBS. The aminated pectin is then reacted with succinimidyl-3-formylsalicylic acid ester prepared as follows. To 0.49 g of 3-formylsalicylic acid (3 mmoles) and 0.42 g of NHS (3.5 mmoles) dissolved in 10–15 ml of DMF, 1.28 g of CMC (3 mmoles) are added and left to react for 5 hours at room temperature protected from moisture. To this reaction mixture 2.1 ml of 2-mercaptoethanol (30 mmoles) are added to quench the unreacted CMC, and after 10 minutes at room temperature the formed succinimidyl-3-formylsalicylic acid ester (10) is used immediately. (The 3-formylsalicylic acid can be replaced by an equimolar amount of 3-carboxybenzaldehyde, 4-formylphenoxyacetic acid or 4,5-dioxoheptanoic acid).

To 2 g of the aminated pectin, dissolved in 30 ml of 0.1 M MOBS (4-[N-morpholino]butanesulfonic acid) buffer, pH 7.6, add the reaction mixture in DMF containing the succinimidyl 3-formylsalicylic acid ester and the mercaptoethanol, and let react with stirring at room temperature for 6 hours. The 3-formylsalicylic acid-pectin derivative (18) is precipitated with 6–8 volumes of ethanol, and then collected and washed with ethanol to remove excess of reactants. The precipitated pectin derivative is dissolved in a minimal volume of water, dialyzed against water, and lyophilized. The aminated pectin can also be reacted with a succinimidyl carbonate intermediate of a hydroxylated, carbonyl-containing compound, such as 4-hydroxyphenylacetaldehyde, 6-hydroxy-2-naphthoquinone, 4-hydroxybenzaldehyde, 2,4-dihydroxybenzaldehyde, formyldienolone, progesterone, androsterone, prednisolone, or pyridoxal. After mixing the reaction with 6 volumes of ethanol, the aldehyde-containing pectic polysaccharide derivative is then recovered by filtration, dissolved in water, dialyzed against water and lyophilized.

Alternatively, the aminated pectin (17) can be reacted with a compound containing both a free and a protected aldehyde group, like terephthaldehyde monodiethylacetal. The aminated pectin is first reacted with the free aldehyde group to form a stable bond, and subsequently the protected aldehyde is released by mild acid hydrolysis, as described here. To 2 g of aminated pectin suspended in 30 ml of aqueous tetrahydrofuran or another suitable solvent, add 0.43 g of terephthaldehyde monodiethylacetal (2 mmoles), 0.18 g of sodium cyanoborohydride (3 mmoles) and let react overnight with stirring at 40° C. to yield the terephthaldehyde monodiethylacetal derivative of pectin (19). The pectin derivative is precipitated with 6 volumes of ethanol, collected, and washed by filtration with more ethanol. The terephthaldehyde monodiethylacetal pectin derivative is dissolved in a minimum volume of 0.05 M HCl and heated at 100° C. for 15–20 minutes to convert the acetal to the aldehyde form. After hydrolysis the solution of phenylacetaldehyde pectin derivative (20) is brought to neutrality with NaOH dialyzed against water and lyophilized. The aromatic aldehyde content of the pectin derivatives is determined spectrophotometrically as follows: dissolve 5–8 mg of the conjugated pectin in 3 ml of 0.05 N NaOH and scan the UV spectra between 220 and 320 nm against a blank solution containing the same amount of unmodified pectin. The aromatic aldehyde concentration of the pectin derivative is calculated using the extinction coefficient of the free aromatic aldehyde as determined in 0.05 M NaOH. The aldehyde content can also be determined spectrophotometrically with MBTH or calorimetrically with Schiff reagent.

Alternatively, the introduction of carbonyl containing compounds to pectic polysaccharides can be carried out in organic solvents. In one example, CMC, NHS, and a 10-fold excess of a diamine with respect to CMC are added to anhydrous lyophilized pectin (H⁺ form) suspended in DMF-pyridine (6:4, v/v) and the mixture is left to react with stirring at room temperature overnight. The number of amine groups per glycosyl residue can be selected by using a limiting amount of CMC in the presence of an excess of diamine ligand. Separation of the aminated polysaccharide from the other reactants is accomplished by precipitating it with 6–8 volumes of ethanol. The ethanol-washed, precipitated, aminated pectin is dissolved in water and lyophilized to yield a powdery product easy to resuspend in DMF-pyridine. The aminated pectin is reacted in DMF-pyridine with either (i) a succinimidyl ester of a carboxylated carbonyl-containing compound, such as 4,5-dioxoheptanoic acid, 3- or 5-formylsalicylic acid, 4-formylcinnamic acid, or 3- or 4-carboxybenzaldehyde, or (ii) the succinimidyl carbonate intermediates of a hydroxylated, carbonyl-containing compound, such as 2,4-dihydroxybenzaldehyde, 4-hydroxybenzaldehyde, 4-hydroxyphenylacetaldehyde, 4'-hydroxyacetophenone, 6-hydroxy-2-naphthoquinone, formyldienolone, progesterone, androsterone, prednisolone, pyridoxal. The aldehyde-containing pectic polysaccharide derivative is then recovered by filtration after mixing the reaction with 6 volumes of ethanol, dissolved in water, dialyzed against water and lyophilized.

D. Addition of Imine-forming Compounds to Amino Groups of Chitin Derivatives

The insolubility of chitin in most solvents hinders the addition of imine-forming compounds to it. However, introduction of carbonyl carrying compounds into the water-soluble chitosan yields water-insoluble gels, which are presumably the result of cross-linking by Schiff-bases between the glucosamine's amine groups and the carbonyl groups from different polysaccharide chains. These obstacles are avoided by use of water-soluble chitin derivatives in which about 85% of the amine groups are N-acetylated, such as glycol chitin (6-O-hydroxypropyl chitin or 6-O-hydroxyethyl chitin) in which primary hydroxyls of the glucosamine are hydroxyethylated. Scheme 5 illustrates this procedure.

SCHEME 5
Addition of imine-forming compounds to glycol chitin

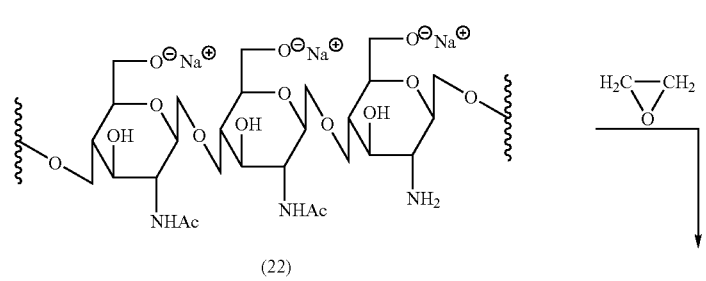

(22)

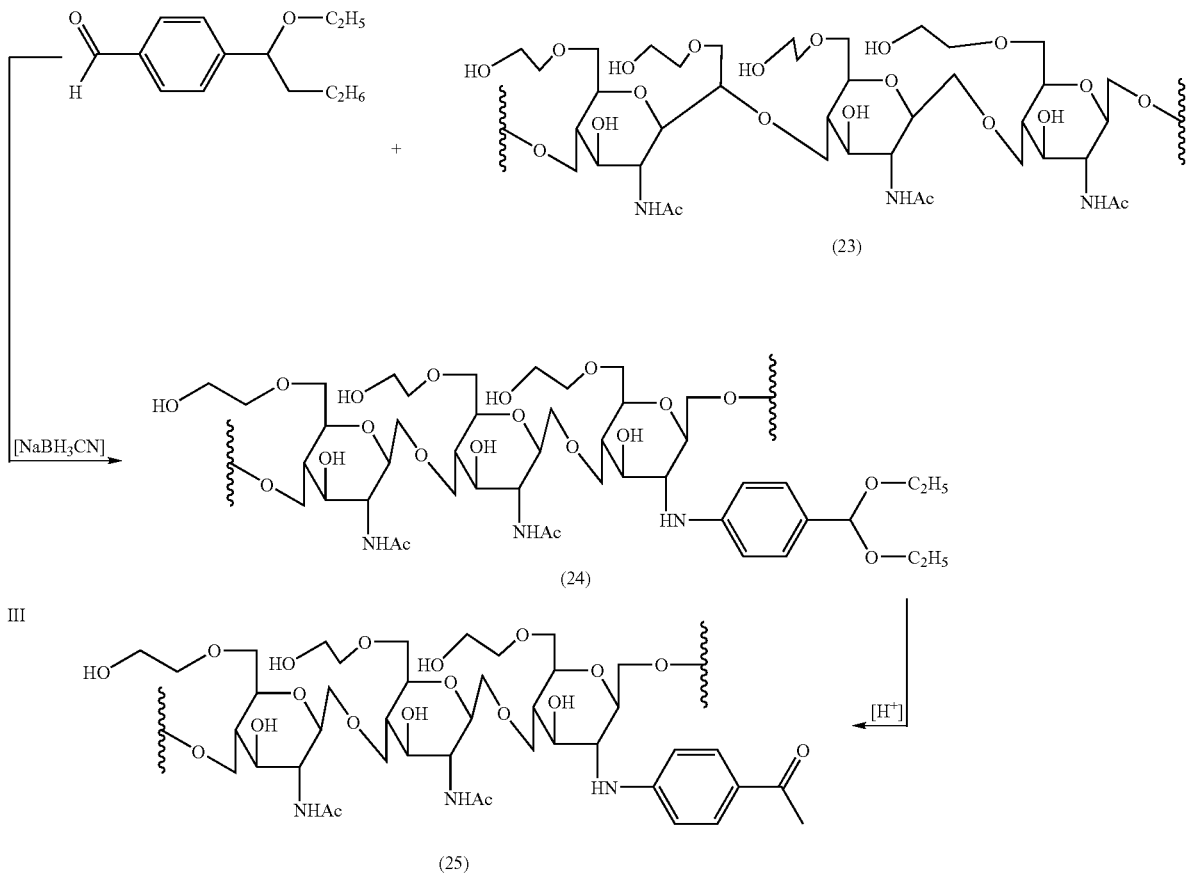

In one embodiment, glycol chitin is prepared as follows. To 5 g of finely ground chitin (22) (equal to 21.25 mmoles of N-acetyl glucosamine and 3.75 mmoles glucosamine) suspended in 30 ml of 42% NaOH for 2 hours at room temperature, add with stirring 70 ml of an ice-water mixture to yield a highly viscous dispersion of alkaline-chitin. To this dispersion, 5 g of ethylene oxide (114 mmoles) are added by bubbling into the solution while stirring for 1–2 hours at 30–35 °C. The glycol chitin (23) is then precipitated with 6 volumes of 80% ethanol, washed on glass filter paper with 80% ethanol, dissolved in water, dialyzed against water, lyophilized and the content of free amine groups determined colorimetrically with TNBS. To 1.7–2 g of lyophilized glycol chitin (about 1.5 mmoles of glucosamine) dissolved/suspended in 40 ml of water add 40 ml of pyridine containing 1.60 g of terephthaldehyde monodiethylacetal (7.5 mmoles), 0.4 g sodium cyanoborohydride (6 mmoles) and let react for 4 hours at room temperature. Precipitate the terephthaldehyde monodiethylacetal derivative of glycol chitin (24) with 4–6 volumes of ethanol, resuspend the precipitate and wash it with 80% ethanol to remove any excess of reactants. Dissolve the glycol chitin derivative (24) in 40–50 ml of 0.05 M HCl and heat at 100° C. for 20–30 minutes to release the aldehyde groups to yield the benzaldehyde derivative of glycol chitin (25). The benzaldehyde content of the glycol chitin derivative is determined spectrophotometrically as follows: dissolve 5–8 mg of the glycol chitin derivative in 4 ml of 0.05 M KOH and read the UV spectra between 220 and 320 nm using as a blank a solution of equal concentration of glycol chitin in 0.05 M KOH. Calculate the incorporated benzaldehyde using the extinction coefficient for this compound determined in 0.05 M KOH. The aldehyde content can also be determined either spectrophotometrically with MBTH or colorimetrically with Schiff reagent.

In another embodiment, described in Scheme 6, glycol chitin (23), formed as described above, is reacted with succinimidyl-5-formylsalicylic acid ester (10), which is prepared as follows. To 0.5 g of 3-formylsalicylic acid (3 mmoles) and 0.42 g of NHS (3.5 mmoles) dissolved in 10–15 ml of DMF, add 1.28 g of CMC (3 mmoles), and let react at room temperature for 5–6 hours protected from moisture. To this reaction mixture add 2.1 ml of p-mercaptoethanol (30 mmoles) to quench the unreacted CMC, mix and react for 10 minutes at room temperature and use the succinimidyl-5-formylsalicylic acid ester immediately. The 5-formylsalicylic acid can be replaced by an equimolar amount of another carboxylated carbonyl-containing compound, such as 4,5-dioxoheptanoic acid, 4-formylcinnamic acid, 3-carboxybenzaldehyde or 4-formylphenoxyacetic acid). To the glycol chitin (1.7–2 g) dissolved in 40 ml of 0.1 M MOBS buffer, pH 7.6, add with stirring the DMF containing the succinimidyl-5-formylsalicylic acid ester and the mercaptoethanol, and let react with stirring at room temperature for 4–6 hours. The 3-formylsalicylic acid derivative of glycol chitin (26) is precipitated with 6 volumes of ethanol and washed with 80% ethanol to remove excess reactants. The precipitated glycol chitin derivative is dissolved in 50–60 ml of water, dialyzed against water, and lyophilized. The 3-formylsalicylic acid content of the glycol chitin derivative is determined spectrophotometrically as follows: dissolve 5–8 mg of the glycol chitin derivative in 4 ml of 0.05 M KOH and read the UV spectra between 220 and 320 nm using as a blank a solution of equal concentration of unmodified glycol chitin in 0.05 M KOH. Calculate the incorporated 3-formylsalicylate using the extinction coefficient for this compound as determined in 0.05 M KOH. The aldehyde content can also be determined either colorimetrically with Schiff reagent or spectrophotometrically with MBTH.

In addition to the procedures described here, other methods, such as the use of glycidyl ethers, activated halogens, and others, can be used to conjugate carbonyl-containing compounds to the glycosyl residues of polysaccharides. See, for example, Maron et al., *Biochim. Biophys. Acta* 278:243 (1972) and Erlanger et al., *J. Biol. Chem.* 228:713 (1957).

Other useful carbohydrate-containing compounds that are recognized by APCs surface receptors include chitins and dextrans which are of animal and bacterial origin respectively. Examples of suitable carbohydrate-containing compounds are bacterial teichoic acids and their derivatives, bacterial lipopolysaccharides, lipid A, and their derivatives.

Conjugation of compounds carrying imine-forming carbonyl groups to non-adjuvant carbohydrate-containing products is contemplated to be useful in providing intrinsic adjuvanticity to these products and to increase the efficacy of preventive immunizations. Examples of these products are polysaccharides from streptococci, staphylococci, and other bacteria that are used as vaccine antigens.

SCHEME 6
Addition of imine-forming compounds to glycol chitin

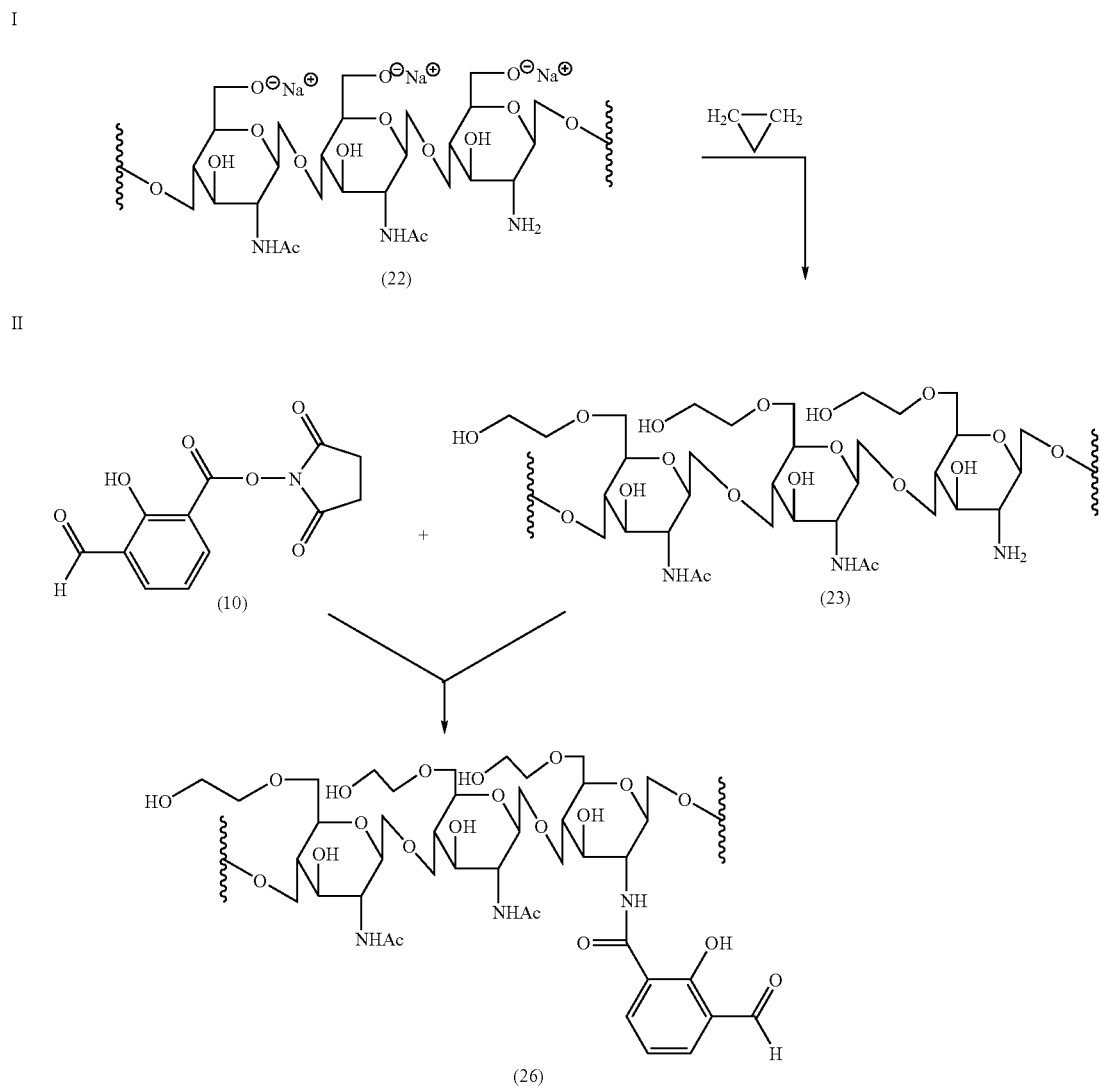

Pharmaceutical and Veterinary Compositions and Methods of Using

In a further aspect, a conjugate of the present invention, for example a compound of Formula I or a physiologically acceptable salt thereof, may be used for the treatment of diseases where there is a defect in the immune system and/or an ineffective host defense mechanism, or to enhance activity to the immune system above normal levels.

A compound of the invention or a physiologically acceptable salts thereof may administered for the treatment or prophylaxis of immunodeficient mammals alone or combination with other therapeutic agents, for example, with other antiviral agents, or with other anticancer agents.

A conjugate of the present invention, for example a compound of Formula I and physiologically acceptable salts thereof may be administered for the treatment or prophylaxis of immunodeficient mammals alone or in combination with other therapeutic agents, for example, with other antiviral agents, or with other anticancer agents.

Immune adjuvants are compounds which, when administered to an individual or tested in vitro, increase the immune response to an antigen in a subject or in a test system to which the antigen is administered.

By an "effective amount" is meant an amount of a conjugate of the present invention that will restore immune function to substantially normal levels, or increase immune function above normal levels in order to eliminate infection.

By potentiation of an immune response is meant restoration of a depressed immune function, enhancement of a normal immune function, or both. Immune function is defined as the development and expression of humoral (antibody-mediated) immunity, cellular (T-cell-mediated) immunity, or macrophage and granulocyte mediated resistance.

In this specification the term "immunodeficient patient" is employed to describe patients with a deficient or defective immune system. An immunodeficient patient can be characterized by means of a T-lymphocyte proliferation assay. Using this assay immunodeficient patients are characterized by a reduced ability of the T-cells to respond to stimulation by mitogens. An example of a mitogen commonly used in this assay is phytohaemagglutinin (PHA).

Immunodeficiency and immunosuppression are thought to occur in many clinical situations where there are lesions in signaling to lymphocytes, particularly T-cells that orchestrate the immune response. T-cells require two signals in order to initiate an effective immune response:

(i) occupation of the specific T-cell receptor for antigen, and (ii) stimulation through costimulatory receptors.

In the absence of signal (ii), T-cells fail to respond and may also become chronically paralyzed or anergic. Persistent viral and bacterial infections and neoplastic disease can produce T-cell hyporesponsiveness by interfering in various ways with the delivery of secondary signals and in this way evade the immune response. The conjugates of the present invention appear to work by substituting or otherwise compensating for deficient costimulatory signals to T-cells.

Recent studies (Rhodes, J., *Immunology Today* 17:436 (1996)) have shown that exogenous Schiff-base-forming compounds can substitute for natural donors of carbonyl groups and provide a costimulatory signal to CD4 T helper (Th) cells. In a related study (Zheng, B. et al., *Science*, 256:1560 (1992)), treatment of APCs with galactose oxidase to form new aldehyde groups resulted in an adjuvant effect when administered with an antigen to mice.

These findings stress the role of Schiff-base forming compounds as stimulators of the immune system. During interaction between an APC and Th-cell there is a transient formation of a Schiff-base between a specialized APC's carbonyl groups and the Th-cell's amino groups located on still undefined cell-surface-receptors. Consequences of the Schiff-base formation are: the biasing of the immune system toward a Th1-type response with an increase in the IL-2 and IFN-γproduction in Th-cells, and the enhancement of the CTL response. Schiff-base forming compounds appear to work by bypassing the co-stimulatory pathway involving the CD-28 receptor on Th-cells and the B7-1 receptor present on APCs.

There are a variety of circumstances in which the immune system may be defective or deficient. For example immune system deficiency is common in immature or premature infants (neonates). It may also result from suppression by certain drugs which may be deliberate e.g. as a side-effect of cancer chemotherapy. Disordered growth of one or more constituent parts of the immune system, e.g. as in certain forms of cancer, may also result in immunodeficiency. Immune deficiency can also be caused by viral infections, including human immunodeficiency virus (HIV).

A further aspect of the present invention provides a method of treating immunodeficient patients, which comprises administering to a mammal an effective amount of a conjugate of the present invention, for example a compound of Formula I, or a physiologically acceptable salt thereof.

A further aspect of the present invention provides for the use of a conjugate of the present invention, for example a compound of Formula I or a physiologically acceptable salt thereof for the treatment and/or prophylaxis of acute and chronic viral infections.

Examples of acute viruses against which immunopotentiatory therapy with a conjugate of the present invention, for example a compound of Formula I or a physiologically acceptable salt thereof may be used, preferably in conjunction with an antiviral agent, are:

herpes viruses, influenza viruses, parainfluenza viruses, adenoviruses, coxsakie viruses, picoma viruses, rotaviruses, hepatitis A virus, mumps virus, rubella virus, measles virus, pox viruses, respiratory syncytial viruses, papilloma viruses, and enteroviruses, arenavirus, rhinoviruses, poliovirus, Newcastle disease virus, rabies virus, and arboviruses.

Examples of chronic viral infections against which immunopotentiatory therapy with conjugates of the present invention may be used are persistent herpes virus infections, Epstein Barr virus infection, persistent rubella infections, papillovirus infections, hepatitis virus infections and human immunodeficiency virus infections.

The conjugates of the invention can be employed alone or in combination with other therapeutic agents for the treatment of the above infections or conditions. Combination therapies according to the present invention comprise the administration of at least one conjugate of the present invention, for example a compound of the Formula I or a physiologically acceptable salt thereof and at least one other pharmaceutically active ingredient. The pharmaceutically active ingredient(s) and compounds of the present invention may be administered together or separately and, when administered separately this may occur simultaneously or sequentially in any order. The amounts of the pharmaceutically active ingredient(s) and compounds of the present invention and the relative timings of administration will be selected in order to achieve the desired combined therapeutic effect. Preferably the combination therapy involves the administration of one compound of the present invention and one of the agents mentioned herein below.

Examples of such further therapeutic agents include agents that are effective for the treatment of HIV infections or associated conditions such as 3'-azido-3'-deoxythymidine (zidovudine), other 2',3'-dideoxynucleosides such as 2',3'-dideoxycytidine, 2',3'-dideoxyadenosine and 2',3'-dideoxyinosine, carbovir, acyclic nucleosides (for example, acyclovir), 2',3'-didehydrothymidine, protease inhibitors such as N-tert-butyl-decahydro-2-[-2(R)-hydroxy-4-phenyl-3(S)-[[N-2-quinolylcarbonyl)-L-asparginyl]butyl]-(4aS,8aS)-isoquinoline-3(S)-carboxamide (Ro31-8959), oxathiolan nucleoside analogs such as cis-1-(2-hydroxymethyl)-1,3-oxathiolan-5-yl)-cytosine or cis-1-(2-(hydroxymethyl)-1,3-oxathiolan-5-yl)-5-fluoro-cytosine, 3'-deoxy-3'-fluorothymidine, 2',3'-dideoxy-5-ethynyl-3'-fluorouridine, 5-chloro-2',3'-dideoxy-3'-fluorouridine, Ribavirin, 9-[4-hydroxy-2-(hydroxymethyl)but-1-yl]guanine (H2G), TAT inhibitors, such as 7-chloro-5-(2-pyrryl)-3H-1,4-benzodiazepin-2(H)-one (Ro5–3335), or 7-chloro-1,3-dihydro-5-(1H-pyrrol-2-yl)-3H-1,4-benzodiazepin-2-amine (Ro24–7429) interferons such as α-interferon, renal excretion inhibitors such as probenecid, nucleoside transport inhibitors such as dipyridamole; pentoxifylline, N-acetylcysteine, precession, α-trichosanthin, phosphonoformic acid, as well as immunomodulators such as interleukin II, granulocyte macrophage colony stimulating factors, erythropoetin, soluble CD4 and genetically-engineered derivatives thereof. Examples of such further therapeutic agents which are effective for the treatment of HBV infections include carbovir, oxathiolan nucleoside analogs such as cis-1-(2-hydroxymethyl)-1,3-oxathiolan-5-yl)cytosine or cis-1-(2-(hydroxymethyl)-1,3-oxathiolan-5-yl)-5-fluorocytosine, 2',3'-didedoxy-5-ethynyl-3'-fluorouridine, 5-chloro-2',3'-didedoxy-3'-fluorouridine, 1-(β-D-arabinofuranosyl)-5-propynyluracil, acyclovir and interferons, such as α-interferon.

In another aspect the present invention provides the use of a conjugate of the present invention, for example a compound of Formula I or a physiologically acceptable salt thereof, for the manufacture of a medicament for the treatment and/or prophylaxis of *Pneumocystis carinii* infections in mammals.

In yet a further aspect the present invention provides for the use of a conjugate of the present invention, for example a compound of Formula I or a physiologically acceptable salt thereof to treat conditions resulting from relative T-cell deficiencies such as DiGeorge Syndrome, fungal infections, mycoplasma infections, tuberculosis, leprosy, and systemic lupus erythemotosus.

In another aspect of the present invention provides for the use of a conjugate of the present invention, for example a compound of Formula I or a physiologically acceptable salt thereof for the manufacture of a medicament for the treatment and/or prophylaxis of cancer in mammals.

Examples of forms of cancers particularly suitable for treatment with compounds the present invention are: melanoma, breast cancer, colon cancer, cancer of the head and neck, gastric cancer, renal cancer, laryngeal cancer, rectal cancer, and non-Hodgkins lymphoma. Cancers that express turnout specific antigens or antigens rarely expressed or expressed at very low density on normal cells, are likely therapeutic targets. Cancers which contain tumor specific cytotoxic T-cells which are anergic or otherwise ineffective are likely targets for therapy. Surgically resected tumors where there is a high risk of recurrence are also suitable for therapy with compounds of the present invention.

A further aspect of the present invention provides for the use, as a vaccine adjuvant, of a conjugate of the present invention, for example a compound of Formula I or a physiologically acceptable salt thereof. A vaccine may therefore be prepared by formulating an antigenic component with a conjugate of the present invention.

Compounds of the present invention may be administered to a human recipient by a route selected from oral, parenteral (including subcutaneous, intradermal, intramuscular and intravenous), rectal and inhalation. The size of an effective dose of a compound will depend upon a number of factors including the identity of the recipient, the type of immunopotentiation involved, the severity of the condition to be treated and the route of administration, and will ultimately be at the discretion of the attendant physician.

The effective dose will generally be in the range of 0.03 to 250 mg per individual, and most preferably between about 0.05 to about 100 mg per dose.

Immune stimulators are preferably administered only once or twice a week, and in some cases, less frequently. Frequency and length of treatment vary among species and individuals.

While it is possible for the compounds of the present invention to be administered as the raw chemical it is preferable to present them as a pharmaceutical formulation preparation. The formulations of the present invention comprise a compound of the present invention, together with one or more acceptable carriers therefor and optionally other therapeutic ingredients. The carrier(s) must be acceptable in the sense of being compatible with the other ingredients of the formulation and not deleterious to the recipient thereof.

Immune adjuvants are compounds which, when administered to an individual or tested in vitro, increase the immune response to an antigen in a subject or in a test system to which the antigen is administered. Some antigens are weakly immunogenic when administered alone or are toxic to a subject at concentrations that evoke useful immune responses in a subject. An immune adjuvant can enhance the immune response of the subject to the antigen by making the antigen more strongly immunogenic. The adjuvant effect can also result in the ability to administer a lower dose of antigen to achieve a useful immune response in a subject.

The immunogen-inducing activity of compounds and compositions of the present invention can be determined by a number of known methods. The increase in titer of antibody against a particular antigen upon administration of a composition of the present invention can be used to measure immunogenic activity. (Dalsgaard, K. *Acta Veterinia Scandinavica* 69:1–40 (1978)). One method requires injecting CD-1 mice intradermally with a test composition that includes one or more exogenous antigens. Sera is harvested from mice two weeks later and tested by ELISA for anti-immunogen antibody.

Compositions of the invention are useful as vaccines to induce active immunity towards antigens in subjects. Any animal that may experience the beneficial effects of the compositions of the present invention within the scope of subjects that may be treated. The subjects are preferably mammals, and more preferably humans.

Conjugates of the present invention can be employed as a sole adjuvant, or alternatively, can be administered together with other adjuvants. Such adjuvants useful with the present invention include oil adjuvants (for example, Freund's Complete and Incomplete), saponins, modified saponins, liposomes, mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from *Mycobacterium tuberculosis*, as well as substances found in *Corynebacterium parvum*, *Bordetella pertussis*, and members of the genus *Brucella*), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained from natural or recombinant sources according to methods known to those skilled in the art. When obtained from recombinant sources, the non-saponin adjuvant may comprise a protein fragment comprising at least the immunogenic portion of the molecule. Other known immunogenic macromolecules which can be used in the practice of the invention include, but are not limited to, polysaccharides, tRNA, non-metabolizable synthetic polymers such as polyvinylamine, polymethacrylic acid, polyvinylpyrrolidone, mixed polycondensates (with relatively high molecular weight) of 4',4-diaminodiphenyl-methane-3, 3'-dicarboxylic acid and 4-nitro-2-aminobenzoic acid (See Sela, M., *Science* 166:1365–1374 (1969)) or glycolipids, lipids or carbohydrates.

The conjugates of the present invention exhibit adjuvant effects when administered over a wide range of dosages and a wide range of ratios to one or more particular antigens being administered.

The conjugates can be administered either individually or admixed with other substantially pure adjuvants to achieve an enhancement of immune response to an antigen.

The conjugates of the present invention can be utilized to enhance the immune response to one or more antigens. Typical antigens suitable for the immune-response provoking compositions of the present invention include antigens derived from any of the following: viruses, such as influenza, feline leukemia virus, feline immunodeficiency virus, HIV-1, HIV-2, rabies, measles, hepatitis B, or hoof and mouth disease; bacteria, such as anthrax, diphtheria, Lyme disease, or tuberculosis; or protozoans, such as *Babeosis bovis* or *Plasmodium*. The antigen can be proteins, peptides, polysaccharides, or mixtures thereof. The proteins and peptides may be purified from a natural source, synthesized by means of solid phase synthesis, or may be obtained means of recombinant genetics.

The conjugates of the present invention can also be administered alone to potentiate the immune system for treatment of chronic infectious diseases, especially in immune compromised patients. Examples of infectious diseases for which conjugates of the present invention can be employed for therapeutic or prophylactic treatment are described in U.S. Pat. No. 5,508,310. Potentiation of the immune system by saponin conjugates can also be useful as a preventative measure to limit the risks of nosocomial and/or post-surgery infections.

Administration of the compounds useful in the method of present invention may be by parenteral, intravenous, intramuscular, subcutaneous, intranasal, or any other suitable means. The dosage administered may be dependent upon the age, weight, kind of concurrent treatment, if any, and nature of the antigen administered. In general, the saponin/antigen conjugates may be administered over a wide range of dosages and a wide range of ratios to the antigen being administered. The initial dose may be followed up with a booster dosage after a period of about four weeks to enhance the immunogenic response. Further booster dosages may also be administered.

The conjugates of the present invention may be employed in such forms as capsules, liquid solutions, emulsions, suspensions or elixirs for oral administration, or sterile liquid forms such as solutions, emulsions or suspensions. Any inert carrier is preferably used, such as saline, or phosphate-buffered saline, or any such carrier in which the compounds used in the method of the present invention have suitable solubility properties for use in the methods of the present invention.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A polysaccharide conjugate consisting essentially of:
   (i) a polysaccharide having a minimum of two saccharides and which is selected from the group consisting of β-glucans, mannans, pectic polysaccharides and 2-acetamido glucan polysaccharides; and
   (ii) one or more molecules having an aldehyde or ketone group; wherein said one or more molecules are the same or different, and are selected from the group consisting of $C_{6-10}$ aryl aldehydes, $C_{6-10}$ aryl($C_{1-4}$ alkyl)aldehydes, $C_{1-4}$ alkyl($C_{6-10}$)aryl, aryl ketones, wherein said aryl ketone contains said ketone group as a substituent attached to an aryl moeity selected from the group consisting of thiophene, furan, benzothiophene, benzofuran, pyridine, quinoline, pyridazine, pyrimidine, pyrazole, imidazole, 1,2,3-triazole, 1,2,4-triazole, isoxazole and oxazole wherein said aldehyde or ketone group is capable of reacting with an amino group to form an imine;
   wherein polysaccharide (i) is attached to molecules (ii) through (iii) a direct covalent bond or covalently via a bifunctional linker in a manner that keeps the aldehyde or ketone group intact; or a pharmaceutically acceptable salt thereof.

2. The polysaccharide conjugate of claim 1, wherein said polysaccharide is a B-glucan, pectic polysaccharide or mannan.

3. A pharmaceutical composition comprising,
   a polysaccharide conjugate of claim 1,
   and a pharmaceutically acceptable carrier or diluent.

4. A polysaccharide conjugate consisting essentially of:
   (i) a polysaccharide having a minimum of two saccharides and which is selected from the group consisting of β-glucans and mannans; and
   (ii) one or more molecules having an aldehyde or ketone group; wherein said one or more molecules are the same or different, and are selected from the group consisting of aryl aldehydes, aryl ketones, heteroaryl ketones, and heteroaryl aldehydes, wherein said aldehyde or ketone group is capable of reacting with an amino group to form an imine;
   wherein polysaccharide (i) is attached to molecules (ii) through (iii) a direct covalent bond or covalently via a bifunctional linker or residue thereof in a manner that keeps the aldehyde or ketone group intact, wherein said bifunctional linker or residue thereof is selected from the group consisting of:
   $H_2N$—$(CH_2)_r$—$NH_2$, where r is from 2 to 12,
   $HO$—$(CH_2)_r$—$NH_2$, where r is from 2 to 12,
   $HS$—$(CH_2)_r$—$NH_2$, where r is from 2 to 12,
   $H$—$(O$—$CH_2\text{-}CH_2)_n$—$OH$, where n is 1–4, ethylenediamine,
1,4-butanediamine,
spermidine,
3,3'-diaminodipropylamine,
N-(2-aminoethyl)-1,3-propanediamine,
2-(4-aminophenyl)ethylamine,
—NH—(CH$_2$)$_r$—NH—, where r is from 2–5,
—O—(CH$_2$)$_r$—NH—, where r is from 2–5,
—O—CH$_2$—CH$_2$—O—CH$_2$—CH$_2$—O—,
—S—(CH$_2$)$_r$—C(O)—, where r is from 1–5,
—S—(CH$_2$)$_r$—NH—, where r is from 2–5,
—S—(CH$_2$)$_r$—O—, where r is from 1–5,
—O—CH$_2$—CH(OH)—CH$_2$—S—CH$_2$—CH$_2$—NH—,
—S—CH$_2$—C(O)—NH—CH$_2$—CH$_2$—NH—, and
—NH—O—C(O)—CH$_2$—CH$_2$—O—P(O$_2$H)—,
or a pharmaceutically acceptable salt thereof.

5. The polysaccharide conjugate of claim 1, wherein said molecules having an aldehyde or ketone group are bound to said polysaccharide via a direct covalent bond.

6. The polysaccharide conjugate of claim 1, wherein said molecules having an aldehyde or ketone group are bound to said polysaccharide via a residue of a bifunctional linker molecule.

7. The polysaccharide conjugate of claim 1, wherein said molecules having an aldehyde or ketone group are selected from the group consisting of mono- and di-substituted C$_{6-10}$ arylaldehydes, C$_{6-10}$ aryl(C$_{1-4}$)alkylaldehydes, and mixtures thereof.

8. The polysaccharide conjugate of claim 1, wherein said molecules having an aldehyde or ketone group are phenyl or naphthyl substituted by a formyl or formyl(C$_{1-4}$)alkyl substituent.

9. The polysaccharide conjugate of claim 8, wherein said substituted phenyl or napthyl molecules contain one or two additional substituents independently selected from the group consisting of halo, hydroxy, C$_{1-4}$ alkyl, C$_{1-4}$ alkoxy, trifluoromethyl, and benzyloxy.

10. The polysaccharide conjugate of claim 1, wherein said molecules having an aldehyde or ketone group are benzaldehyde or naphthaldehyde, substituted by one or two of hydroxy and halo.

11. The polysaccharide conjugate of claim 10, wherein said molecules having an aldehyde or ketone group is benzaldehyde.

12. The polysaccharide conjugate of claim 1, wherein said molecules having an aldehyde or ketone group is 3-carboxybenzaldehyde or 4-carboxybenzaldehyde.

13. The polysaccharide conjugate of claim 1, wherein said molecule having an aldehyde or ketone group is selected from the group consisting of 2,3-, 2,4–2,5-, and 3,4-dihydroxybenzaldehyde, 5-chloro-2-hydroxybenzaldehyde, vanillin, ethyl vanillin, naringenin, 3- and 4-hydroxybenzaldehyde, or 4-hydroxyphenylacetaldehyde; hydroxy substituted C$_{1-4}$alkyl (C$_{6-10}$)aryl ketones, and hydroxy substituted aryl ketones; 2-hydroxyacetophenone, 3-hydroxyacetophenone, 4-hydroxyacetophenone, and 6-hydroxy-1,2-naphthoquinone; thiophene, furan, benzothiophene, benzofuran, pyridine, quinoline, pyridazine, pyrimidine, pyrazole, imidazole, 1,2,3-triazole, 1,2,4-triazole, isoxazole, or oxazole, each having a keto, formyl or formyl(C$_{1-4}$) substituent, and optionally including an additional halo or hydroxy substituent, if these can be accommodated by available ring carbon atoms; pyridoxal, 2-thiophenecarboxaldehyde, and 3-thiophenecarboxaldehyde.

14. The polysaccharide conjugate of claim 1, wherein said polysaccharide is selected from the group consisting of: β-glucans, mannans, and esters, sulfonates, sulfates, phosphates, ethers, and cross-linked derivatives thereof.

15. The polysaccharide conjugate of claim 1, wherein said polysaccharide is a β-glucan having a backbone chain of (1→3)-linked β-D-glucopyranosyl units and which has β-D-glucopyranosyl units attached by (1→6) linkages, and a molecular weight of between 1,000 to 500,000, and wherein said β-glucan is optionally modified by the addition of one or more anionic, cationic or non-ionic groups.

16. The polysaccharide conjugate of claim 1, wherein said polysaccharide is a β-mannan comprising (1→4) polymannose having a terminus reducing mannosyl residue, or the acetylation product thereof.

17. A pharmaceutical composition comprising,
a polysaccharide conjugate of claim 1,
and a pharmaceutically acceptable carrier or diluent.

18. The polysaccharide conjugate of claim 1, wherein said polysaccharide has a minimum of seven saccharides.

19. The polysaccharide conjugate of claim 15, wherein said molecular weight is between 5,000 to 500,000.

* * * * *